United States Patent
Cavazzuti et al.

(10) Patent No.: US 7,491,749 B2
(45) Date of Patent: *Feb. 17, 2009

(54) AT LEAST ONE POLYAMIDE POLYMER IN A COSMETIC COMPOSITION COMPRISING AT LEAST ONE SOLID SUBSTANCE HAVING A MELTING POINT OF 45 DEGREES C. OR GREATER

(75) Inventors: Roberto Cavazzuti, Westfield, NJ (US); Véronique Ferrari, Maisons-Alfort (FR); Brian Mattox, Plainfield, NJ (US); Carlos O. Pinzon, Hackensack, NJ (US); Paul Thau, Berkeley Heights, NJ (US)

(73) Assignee: L'Oreal, Paris (FR)

( * ) Notice: Subject to any disclaimer, the term of this patent is extended or adjusted under 35 U.S.C. 154(b) by 816 days.

This patent is subject to a terminal disclaimer.

(21) Appl. No.: 10/182,830

(22) PCT Filed: Dec. 12, 2001

(86) PCT No.: PCT/IB01/02804

§ 371 (c)(1),
(2), (4) Date: Jan. 21, 2003

(87) PCT Pub. No.: WO02/47608

PCT Pub. Date: Jun. 20, 2002

(65) Prior Publication Data

US 2004/0141941 A2    Jul. 22, 2004

(51) Int. Cl.
*A61K 7/00* (2006.01)
*A61K 7/027* (2006.01)
*A61K 7/031* (2006.01)
*A61K 7/032* (2006.01)

(52) U.S. Cl. .............. 514/772.3; 514/772.4; 514/772.6; 514/784; 514/844

(58) Field of Classification Search .................. 424/707, 424/401
See application file for complete search history.

(56) References Cited

U.S. PATENT DOCUMENTS

| | | |
|---|---|---|
| 2,379,413 A | 7/1945 | Bradley |
| 2,450,940 A | 10/1948 | Cowan et al. |
| 2,463,264 A | 3/1949 | Graenacher |
| 2,662,068 A | 12/1953 | Floyd |
| 2,663,649 A | 12/1953 | Winkler |
| 2,890,097 A | 6/1959 | Coe |
| 2,962,461 A | 11/1960 | Toussaint et al. |
| 3,086,914 A | 4/1963 | Soloway ............ 167/85 |
| 3,141,787 A | 7/1964 | Goetze et al. |
| 3,148,125 A | 9/1964 | Strianse et al. |
| 3,156,572 A | 11/1964 | Carlick et al. |
| 3,157,681 A | 11/1964 | Fischer |
| 3,255,082 A | 6/1966 | Barton |
| 3,341,465 A | 9/1967 | Kaufman et al. |
| 3,412,115 A | 11/1968 | Floyd et al. |
| 3,615,289 A | 10/1971 | Felton |
| 3,645,705 A | 2/1972 | Miller et al. |
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. |
| 3,969,087 A | 7/1976 | Saito et al. |
| 4,049,792 A | 9/1977 | Elsnau |

(Continued)

FOREIGN PATENT DOCUMENTS

CA        1319306        6/1988

(Continued)

OTHER PUBLICATIONS

English language Derwent abstract of JP A 62061911.

(Continued)

*Primary Examiner*—Marianne Seidel
(74) *Attorney, Agent, or Firm*—Finnegan, Henderson, Farabow, Garrett & Dunner, L.L.P.

(57) ABSTRACT

Cosmetic compositions comprising at least one structuring polymer chosen from polymers of following formula (I):

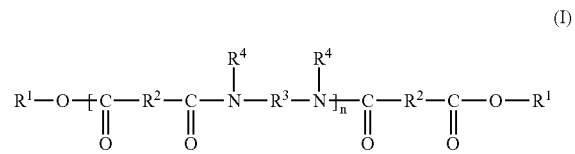

in which n denotes a number of amide units, such that the number of ester groups represents from 10% to 50% of the total number of ester and amide groups; $R^1$ is, in each case, independently an alkyl or alkenyl group having at least 4 carbon atoms; $R^2$ independently represents, in each case, a $C_4$ to $C_{42}$ hydrocarbonaceous group, provided that 50% of the $R^2$ groups represent a $C_{30}$ to $C_{42}$ hydrocarbonaceous group; $R^3$ independently represents, in each case, an organic group provided with at least 2 carbon atoms, with hydrogen atoms and optionally with one or more oxygen or nitrogen atoms; and $R^4$ independently represents, in each case, a hydrogen atom, a $C_1$ to $C_{10}$ alkyl group or a direct bond to $R^3$ or another $R^4$, so that the nitrogen atom to which both $R^3$ and $R^4$ are bonded forms part of a heterocyclic structure defined by $R^4$—N—$R^3$, with at least 50% of the $R^4$ groups representing a hydrogen atom and at least one solid substance that has a melting point of 45° C. or greater.

2 Claims, No Drawings

U.S. PATENT DOCUMENTS

| | | | |
|---|---|---|---|
| 4,051,159 A | 9/1977 | Tsoucalas et al. | |
| 4,062,819 A | 12/1977 | Mains et al. | |
| RE29,871 E | 12/1978 | Papantoniou et al. | |
| 4,128,436 A | 12/1978 | O'Hara et al. | |
| 4,137,306 A | 1/1979 | Rubino et al. | |
| 4,148,875 A | 4/1979 | Barnett et al. | |
| 4,150,002 A | 4/1979 | Drawert et al. | |
| 4,247,411 A | 1/1981 | Vanlerberghe et al. | |
| 4,275,054 A | 6/1981 | Sebag et al. | |
| 4,275,055 A | 6/1981 | Nachtigal et al. | 424/70 |
| 4,278,658 A | 7/1981 | Hooper et al. | |
| 4,279,658 A | 7/1981 | Harvey et al. | |
| 4,337,298 A | 6/1982 | Karim et al. | |
| 4,341,671 A | 7/1982 | Bolze et al. | |
| 4,367,390 A | 1/1983 | Balleys et al. | |
| 4,376,194 A | 3/1983 | Tanaka et al. | |
| 4,387,090 A | 6/1983 | Bolich, Jr. | 424/70 |
| 4,438,240 A | 3/1984 | Tanaka et al. | |
| 4,466,936 A | 8/1984 | Schapel | |
| 4,536,405 A | 8/1985 | Nara et al. | |
| 4,552,693 A | 11/1985 | Hussain et al. | 252/522 |
| 4,571,267 A | 2/1986 | Drawert et al. | |
| 4,620,492 A | 11/1986 | Vogg et al. | |
| 4,655,836 A | 4/1987 | Drawert et al. | |
| 4,663,428 A | 5/1987 | Okitu et al. | |
| 4,699,779 A | 10/1987 | Palinczar | |
| 4,712,571 A | 12/1987 | Remz et al. | |
| 4,724,137 A | 2/1988 | Hoppe et al. | |
| 4,769,285 A | 9/1988 | Rasmussen | |
| 4,806,338 A | 2/1989 | Smith | 424/47 |
| 4,806,345 A | 2/1989 | Bhattacharyya | 424/70 |
| 4,820,765 A | 4/1989 | Whyzmuzis | |
| 4,822,601 A | 4/1989 | Goode et al. | |
| 4,871,536 A | 10/1989 | Arraudeau et al. | 424/59 |
| 4,885,709 A | 12/1989 | Edgar et al. | |
| 4,937,069 A | 6/1990 | Shin | |
| 4,952,245 A | 8/1990 | Iwano et al. | |
| 5,034,219 A | 7/1991 | Deshpande et al. | |
| 5,061,289 A | 10/1991 | Clausen et al. | |
| 5,069,897 A | 12/1991 | Orr | 424/66 |
| 5,073,364 A | 12/1991 | Giezendanner et al. | |
| 5,085,859 A | 2/1992 | Halloran et al. | |
| 5,102,656 A | 4/1992 | Kasat | |
| 5,166,355 A | 11/1992 | Leistner et al. | |
| 5,186,318 A | 2/1993 | Oestreich et al. | 206/37 |
| 5,196,260 A | 3/1993 | Dirschl et al. | |
| 5,223,559 A | 6/1993 | Arraudeau et al. | |
| 5,237,071 A | 8/1993 | Leistner et al. | |
| 5,252,323 A | 10/1993 | Richard et al. | |
| 5,268,029 A | 12/1993 | Demangeon et al. | |
| 5,272,241 A | 12/1993 | Lucarelli et al. | 528/15 |
| 5,290,555 A | 3/1994 | Guthauser et al. | |
| 5,302,398 A | 4/1994 | Egidio et al. | |
| 5,342,894 A | 8/1994 | Robeson et al. | |
| 5,362,482 A | 11/1994 | Yoneyama et al. | |
| 5,372,852 A | 12/1994 | Titterington et al. | |
| 5,389,363 A * | 2/1995 | Snyder et al. | 424/70.7 |
| 5,472,686 A | 12/1995 | Tsubaki et al. | |
| 5,486,431 A | 1/1996 | Tuttle et al. | |
| 5,489,431 A | 2/1996 | Ascione et al. | |
| 5,500,209 A | 3/1996 | Ross et al. | |
| 5,505,937 A | 4/1996 | Castrogiovanni et al. | |
| 5,510,452 A | 4/1996 | Santhanam | 528/291 |
| 5,536,871 A | 7/1996 | Santhanam | 560/196 |
| 5,538,718 A | 7/1996 | Aul et al. | |
| 5,538,793 A | 7/1996 | Inokuchi et al. | |
| 5,540,853 A | 7/1996 | Trinh et al. | 510/101 |
| 5,585,091 A | 12/1996 | Pelzer et al. | |
| 5,603,925 A | 2/1997 | Ross et al. | 424/65 |
| 5,605,651 A | 2/1997 | Balzer | |
| 5,610,199 A | 3/1997 | Cohen et al. | |
| 5,612,043 A | 3/1997 | Deprez et al. | |
| 5,616,331 A | 4/1997 | Allard et al. | |
| 5,618,523 A | 4/1997 | Zysman et al. | 424/70.1 |
| 5,620,693 A | 4/1997 | Piot et al. | |
| 5,628,029 A | 5/1997 | Evoy | |
| 5,645,632 A | 7/1997 | Pavlin | |
| 5,667,770 A | 9/1997 | Szweda et al. | 424/64 |
| 5,679,357 A | 10/1997 | Dubief et al. | 424/401 |
| 5,683,817 A | 11/1997 | Kenmochi | |
| 5,695,747 A | 12/1997 | Forestier et al. | |
| 5,702,519 A | 12/1997 | Nitta et al. | |
| 5,719,255 A | 2/1998 | Heucher et al. | |
| 5,747,625 A | 5/1998 | Furukawa et al. | |
| 5,750,125 A | 5/1998 | Lahanas et al. | |
| 5,750,127 A | 5/1998 | Rokitowski | |
| 5,750,489 A | 5/1998 | Garcia et al. | |
| 5,769,902 A | 6/1998 | Samain | |
| 5,780,517 A | 7/1998 | Cohen et al. | |
| 5,783,657 A | 7/1998 | Pavlin et al. | |
| 5,795,565 A | 8/1998 | Eteve et al. | |
| 5,800,816 A * | 9/1998 | Brieva et al. | 424/63 |
| 5,807,968 A | 9/1998 | Heinrich et al. | |
| 5,830,444 A | 11/1998 | Miguel | |
| 5,830,483 A | 11/1998 | Seidel et al. | |
| 5,837,223 A * | 11/1998 | Barone et al. | 424/64 |
| 5,849,275 A | 12/1998 | Calello et al. | |
| 5,849,278 A | 12/1998 | Piot et al. | |
| 5,849,333 A | 12/1998 | Nordhauser et al. | |
| 5,849,909 A | 12/1998 | Richard et al. | |
| 5,851,517 A | 12/1998 | Mougin et al. | |
| 5,857,903 A | 1/1999 | Ramspeck et al. | |
| 5,858,338 A | 1/1999 | Piot et al. | |
| 5,866,149 A | 2/1999 | Piot et al. | |
| 5,871,764 A | 2/1999 | Diaz et al. | |
| 5,874,069 A | 2/1999 | Mendolia et al. | 424/65 |
| 5,882,363 A | 3/1999 | Spaulding et al. | |
| 5,891,424 A | 4/1999 | Bretzler et al. | |
| 5,897,869 A | 4/1999 | Roulier et al. | 424/401 |
| 5,902,592 A | 5/1999 | Bara et al. | |
| 5,908,631 A | 6/1999 | Arnaud et al. | |
| 5,911,974 A | 6/1999 | Brieva et al. | 424/64 |
| 5,919,441 A | 7/1999 | Mendolia et al. | 424/78.08 |
| 5,925,337 A | 7/1999 | Arraudeau et al. | |
| 5,945,095 A | 8/1999 | Mougin et al. | |
| 5,945,112 A | 8/1999 | Flynn et al. | |
| 5,955,060 A | 9/1999 | Huglin et al. | |
| 5,959,009 A | 9/1999 | Konik et al. | 524/261 |
| 5,961,998 A | 10/1999 | Arnaud et al. | |
| 5,962,452 A | 10/1999 | Haase et al. | |
| 5,965,112 A | 10/1999 | Brieva et al. | 424/64 |
| 5,972,095 A | 10/1999 | Graves et al. | |
| 5,972,354 A | 10/1999 | de la Poterie et al. | |
| 5,972,359 A | 10/1999 | Sine et al. | |
| 5,976,512 A | 11/1999 | Huber | |
| 5,976,514 A | 11/1999 | Guskey et al. | |
| 5,981,680 A | 11/1999 | Petroff et al. | |
| 5,985,298 A | 11/1999 | Brieva et al. | |
| 5,993,787 A | 11/1999 | Sun et al. | |
| 5,998,570 A | 12/1999 | Pavlin et al. | |
| 6,001,980 A | 12/1999 | Borzo et al. | |
| 6,004,567 A | 12/1999 | Marchi-Lemann et al. | |
| 6,007,799 A | 12/1999 | Lee et al. | |
| 6,019,962 A | 2/2000 | Rabe et al. | |
| 6,036,947 A | 3/2000 | Barone et al. | |
| 6,045,782 A | 4/2000 | Krog et al. | |
| 6,045,823 A | 4/2000 | Vollhardt et al. | |
| 6,051,216 A | 4/2000 | Barr et al. | 424/78.35 |
| 6,054,517 A | 4/2000 | Spaulding et al. | |
| 6,060,072 A | 5/2000 | Konik et al. | 424/401 |
| 6,063,398 A | 5/2000 | Gueret | |
| 6,066,328 A | 5/2000 | Ribier et al. | |
| 6,074,654 A | 6/2000 | Drechsler et al. | 424/401 |
| 6,093,385 A | 7/2000 | Habeck et al. | |

| | | | | | | |
|---|---|---|---|---|---|---|
| 6,103,249 | A | 8/2000 | Roulier et al. ............... 424/401 | 2002/0058053 A1 | 5/2002 | Nakanishi et al. |
| 6,106,820 | A | 8/2000 | Morrissey et al. | 2002/0081323 A1 | 6/2002 | Nakanishi et al. |
| 6,111,055 | A | 8/2000 | Berger et al. | 2002/0102225 A1 | 8/2002 | Hess et al. |
| 6,132,745 | A | 10/2000 | Marchi-lemann et al. | 2002/0107314 A1 | 8/2002 | Pinzon et al. |
| 6,156,325 | A | 12/2000 | Farer et al. ................. 424/401 | 2002/0111330 A1 | 8/2002 | Pinzon et al. |
| 6,156,804 | A | 12/2000 | Chevalier et al. | 2002/0114771 A1 | 8/2002 | Nakanishi |
| 6,159,455 | A | 12/2000 | Habeck et al. | 2002/0114773 A1 | 8/2002 | Kanji et al. |
| 6,165,454 | A | 12/2000 | Patel et al. | 2002/0119171 A1 | 8/2002 | Gruning et al. |
| 6,165,971 | A | 12/2000 | Oppenlander et al. | 2002/0120036 A1 | 8/2002 | Pinzon et al. |
| 6,171,347 | B1 | 1/2001 | Kunz | 2002/0122781 A1 | 9/2002 | Pinzon et al. |
| 6,177,523 | B1 | 1/2001 | Reich et al. .................. 525/459 | 2002/0131947 A1 | 9/2002 | Nakanishi |
| 6,180,117 | B1 | 1/2001 | Berthiaume et al. | 2002/0141958 A1 | 10/2002 | Maio et al. |
| 6,180,123 | B1 | 1/2001 | Mondet | 2002/0150602 A1 | 10/2002 | Livoreil et al. |
| 6,190,673 | B1 | 2/2001 | Guskey et al. ............... 424/401 | 2002/0159964 A1 | 10/2002 | Nakanishi et al. |
| 6,197,100 | B1 | 3/2001 | Melbouci | 2002/0168335 A1 | 11/2002 | Collin |
| 6,203,780 | B1 | 3/2001 | Arnaud et al. | 2002/0172696 A1 | 11/2002 | Ferrari |
| 6,203,807 | B1 | 3/2001 | Lemann | 2002/0189030 A1 | 12/2002 | Collin |
| 6,214,326 | B1 | 4/2001 | Dupuis | 2002/0192168 A1 | 12/2002 | Blin et al. |
| 6,214,329 | B1* | 4/2001 | Brieva et al. ................ 424/70.7 | 2003/0012764 A1 | 1/2003 | Collin |
| 6,221,389 | B1 | 4/2001 | Cannell et al. | 2003/0026772 A1 | 2/2003 | Jager-Lezer et al. |
| 6,224,851 | B1 | 5/2001 | Bara | 2003/0044367 A1 | 3/2003 | Simon et al. |
| 6,242,509 | B1 | 6/2001 | Berger et al. | 2003/0086883 A1 | 5/2003 | Feng et al. |
| 6,251,375 | B1 | 6/2001 | Bara | 2003/0129211 A9 | 7/2003 | Livoreil et al. |
| 6,251,409 | B1 | 6/2001 | Hegyi et al. | 2003/0147837 A1 | 8/2003 | Cavazzuti et al. |
| 6,254,876 | B1 | 7/2001 | de la Poterie et al. | 2003/0161807 A1 | 8/2003 | Lemann |
| 6,254,877 | B1 | 7/2001 | de la Poterie et al. | 2003/0161848 A1 | 8/2003 | Ferrari et al. |
| 6,264,933 | B1 | 7/2001 | Bodelin et al. | 2003/0185780 A1 | 10/2003 | Ferrari et al. |
| 6,268,466 | B1 | 7/2001 | MacQueen et al. | 2003/0198613 A1 | 10/2003 | Feng et al. |
| 6,280,846 | B1 | 8/2001 | Darby et al. | 2004/0013625 A1 | 1/2004 | Kanji |
| 6,287,552 | B1 | 9/2001 | Tournilhac et al. | 2004/0028636 A1 | 2/2004 | Collin |
| 6,325,994 | B1 | 12/2001 | Collin et al. | 2004/0042980 A1 | 3/2004 | Kanji et al. |
| 6,348,563 | B1 | 2/2002 | Fukuda et al. | 2004/0086478 A1 | 5/2004 | Ferrari |
| 6,361,764 | B2 | 3/2002 | Richard et al. | 2004/0091510 A1 | 5/2004 | Feng et al. |
| 6,372,235 | B1 | 4/2002 | Livoreil et al. | 2004/0126401 A1 | 7/2004 | Collin |
| 6,376,078 | B1 | 4/2002 | Inokuchi | 2004/0166076 A1 | 8/2004 | Ferrari et al. |
| 6,383,502 | B1 | 5/2002 | Dunshee et al. | 2004/0166133 A1 | 8/2004 | Cavazzuti et al. |
| 6,399,080 | B1 | 6/2002 | Bara | 2004/0247549 A1 | 12/2004 | Lu et al. |
| 6,399,081 | B1 | 6/2002 | Nakanishi et al. | 2005/0008598 A1 | 1/2005 | Lu et al. |
| 6,402,408 | B1* | 6/2002 | Ferrari ........................ 401/64 | 2005/0008599 A1 | 1/2005 | Lu et al. |
| 6,410,003 | B1 | 6/2002 | Bhatia et al. | 2005/0065261 A1 | 3/2005 | Darlington, Jr. et al. |
| 6,423,306 | B2 | 7/2002 | Caes et al. | 2005/0089491 A1 | 4/2005 | Collin |
| 6,423,324 | B1 | 7/2002 | Murphy et al. | 2005/0089505 A1 | 4/2005 | Collin |
| 6,428,773 | B1 | 8/2002 | Oko et al. | 2005/0089541 A1 | 4/2005 | Lacoutiere |
| 6,432,391 | B1 | 8/2002 | Bara | 2005/0191327 A1 | 9/2005 | Yu et al. |
| 6,447,759 | B2 | 9/2002 | Noguchi et al. | | | |
| 6,469,131 | B2 | 10/2002 | Lawson et al. | FOREIGN PATENT DOCUMENTS | | |
| 6,475,500 | B2 | 11/2002 | Vatter et al. | CA | 2003346 | 5/1990 |
| 6,479,686 | B2 | 11/2002 | Nakanishi et al. | DE | 38 39 136 A1 | 5/1990 |
| 6,482,400 | B1 | 11/2002 | Collin | DE | 38 43 892 A1 | 6/1990 |
| 6,491,931 | B1 | 12/2002 | Collin | DE | 42 08 297 A1 | 9/1993 |
| 6,497,861 | B1 | 12/2002 | Wang et al. | DE | 42 34 886 A1 | 4/1994 |
| 6,503,522 | B2 | 1/2003 | Lawson et al. | DE | 195 43 988 A1 | 5/1997 |
| 6,506,716 | B1 | 1/2003 | Delplancke et al. | DE | 197 07 309 A1 | 8/1998 |
| 6,545,174 | B2 | 4/2003 | Habeck et al. | DE | 197 26 184 A1 | 12/1998 |
| 6,552,160 | B2 | 4/2003 | Pavlin | DE | 197 50 246 A1 | 5/1999 |
| 6,649,173 | B1 | 11/2003 | Arnaud et al. | DE | 197 55 649 A1 | 6/1999 |
| 6,682,748 | B1 | 1/2004 | De La Poterie et al. | DE | 198 55 649 A1 | 6/2000 |
| 6,716,420 | B2 | 4/2004 | Feng et al. | DE | 199 51 010 A1 | 4/2001 |
| 6,726,917 | B2 | 4/2004 | Kanji et al. | EP | 0 169 997 B1 | 2/1986 |
| 6,749,173 | B2 | 6/2004 | Heiling | EP | 0 295 886 | 12/1988 |
| 6,761,881 | B2 | 7/2004 | Bara | EP | 0 370 470 B1 | 5/1990 |
| 6,869,594 | B2 | 3/2005 | Ferrari | EP | 0 374 332 A1 | 6/1990 |
| 6,875,245 | B2 | 4/2005 | Pavlin | EP | 0 412 710 B1 | 2/1991 |
| 6,881,400 | B2 | 4/2005 | Collin | EP | 0 444 633 A2 | 9/1991 |
| 6,960,339 | B1 | 11/2005 | Ferrari et al. | EP | 0 507 692 A1 | 10/1992 |
| 6,979,469 | B2 | 12/2005 | Ferrari et al. | EP | 0 517 104 B1 | 12/1992 |
| 2001/0014312 | A1 | 8/2001 | Nakanishi et al. | EP | 0 518 772 A1 | 12/1992 |
| 2001/0014313 | A1 | 8/2001 | Roulier et al. | EP | 0 518 773 A1 | 12/1992 |
| 2001/0028887 | A1 | 10/2001 | Douin et al. | EP | 0 557 196 A1 | 8/1993 |
| 2001/0031280 | A1 | 10/2001 | Ferrari et al. | EP | 0 570 838 B1 | 11/1993 |
| 2001/0033846 | A1 | 10/2001 | Roulier et al. | EP | 0 602 905 B1 | 6/1994 |
| 2002/0010179 | A1 | 1/2002 | Richard et al. | EP | 0 609 132 B1 | 8/1994 |
| 2002/0044918 | A1 | 4/2002 | Bara | | | |

| | | | | | |
|---|---|---|---|---|---|
| EP | 0 623 670 A2 | 11/1994 | FR | 2 811 552 | 1/2002 |
| EP | 0 628 582 B1 | 12/1994 | FR | 2 816 506 | 5/2002 |
| EP | 0 669 323 A1 | 8/1995 | FR | 2 817 739 | 6/2002 |
| EP | 0 673 642 B1 | 9/1995 | FR | 2 817 740 | 6/2002 |
| EP | 0 708 114 A1 | 4/1996 | FR | 2 817 742 | 6/2002 |
| EP | 0 749 746 A1 | 12/1996 | FR | 2 817 743 | 6/2002 |
| EP | 0 749 747 A1 | 12/1996 | FR | 2 819 399 | 7/2002 |
| EP | 0 749 748 A1 | 12/1996 | FR | 2 819 400 | 7/2002 |
| EP | 0 775 483 A1 | 5/1997 | FR | 2 819 402 | 7/2002 |
| EP | 0 775 698 A1 | 5/1997 | GB | 1 117 129 | 6/1968 |
| EP | 0 790 243 A1 | 8/1997 | GB | 1 194 901 | 6/1970 |
| EP | 0 796 851 A1 | 9/1997 | GB | 1 194 902 | 6/1970 |
| EP | 0 797 976 A2 | 10/1997 | GB | 1 220 069 | 1/1971 |
| EP | 0 820 764 A1 | 1/1998 | GB | 1 273 004 | 5/1972 |
| EP | 0 847 752 A1 | 6/1998 | GB | 1 444 204 | 7/1976 |
| EP | 0 863 145 A2 | 9/1998 | GB | 1 539 625 | 1/1979 |
| EP | 0 877 063 B1 | 11/1998 | GB | 2 014 852 A | 9/1979 |
| EP | 0 878 469 A1 | 11/1998 | GB | 2 021 411 A | 12/1979 |
| EP | 0 879 592 A2 | 11/1998 | GB | 2 147 305 A | 5/1985 |
| EP | 0 887 073 A1 | 12/1998 | GB | 2 196 978 A | 5/1988 |
| EP | 0 893 119 B1 | 1/1999 | JP | 50/58242 | 5/1975 |
| EP | 0 923 928 A1 | 6/1999 | JP | 53/043577 | 4/1978 |
| EP | 0 925 780 A1 | 6/1999 | JP | 56/123909 | 9/1981 |
| EP | 0 928 608 A2 | 7/1999 | JP | 56/166276 | 12/1981 |
| EP | 0 930 058 B1 | 7/1999 | JP | 61/065809 | 4/1986 |
| EP | 0 930 060 A1 | 7/1999 | JP | 62061911 | 3/1987 |
| EP | 0 933 376 A2 | 8/1999 | JP | 2/127568 | 5/1990 |
| EP | 0 943 340 A1 | 9/1999 | JP | 02/200612 | 8/1990 |
| EP | 0 958 804 A2 | 11/1999 | JP | 02/207014 | 8/1990 |
| EP | 0 958 805 A2 | 11/1999 | JP | 2/216279 | 8/1990 |
| EP | 0 958 811 A1 | 11/1999 | JP | 3/014683 | 1/1991 |
| EP | 0 959 066 A2 | 11/1999 | JP | 04/346909 | 12/1992 |
| EP | 0 959 091 A1 | 11/1999 | JP | 7/179795 | 7/1995 |
| EP | 0 967 200 A1 | 12/1999 | JP | 7/267827 | 10/1995 |
| EP | 0 976 390 A1 | 2/2000 | JP | 8/225316 | 9/1996 |
| EP | 0 984 025 A2 | 3/2000 | JP | 9/20631 | 1/1997 |
| EP | 1 002 514 A1 | 5/2000 | JP | 09/255560 | 9/1997 |
| EP | 1 031 342 A1 | 8/2000 | JP | 9/295922 | 11/1997 |
| EP | 1 044 676 A2 | 10/2000 | JP | 10/007527 | 1/1998 |
| EP | 1 048 282 A1 | 11/2000 | JP | 10/120903 | 5/1998 |
| EP | 1 053 742 A1 | 11/2000 | JP | 10/212213 | 8/1998 |
| EP | 1 062 944 A1 | 12/2000 | JP | 10/259344 | 9/1998 |
| EP | 1 092 959 A1 | 12/2000 | JP | 11/106216 | 4/1999 |
| EP | 1 064 920 A1 | 1/2001 | JP | 11/335228 | 12/1999 |
| EP | 1 066 814 A1 | 1/2001 | JP | 11/335242 | 12/1999 |
| EP | 1 068 854 A1 | 1/2001 | JP | 11/335254 | 12/1999 |
| EP | 1 068 855 A1 | 1/2001 | JP | 2000038314 A | 2/2000 |
| EP | 1 068 856 A1 | 1/2001 | JP | 2000038316 A | 2/2000 |
| EP | 1 094 919 A1 | 1/2001 | JP | 2000038317 A | 2/2000 |
| EP | 1 086 945 A1 | 3/2001 | JP | 2000038321 A | 2/2000 |
| EP | 1 090 627 A1 | 4/2001 | JP | 2000086427 A | 3/2000 |
| EP | 1 095 959 A2 | 5/2001 | JP | 2000086429 A | 3/2000 |
| EP | 1 114 636 A1 | 7/2001 | JP | 2000086438 A | 3/2000 |
| EP | 1 213 011 A1 | 6/2002 | WO | WO 86/04916 | 8/1986 |
| EP | 1 213 316 A2 | 6/2002 | WO | WO 87/03783 | 7/1987 |
| FR | 1 529 329 | 5/1968 | WO | WO 91/12793 | 9/1991 |
| FR | 2 232 303 | 1/1975 | WO | WO 93/04665 | 3/1993 |
| FR | 2 315 991 | 1/1977 | WO | WO 93/21763 | 11/1993 |
| FR | 2 416 008 | 8/1979 | WO | WO 93/23008 | 11/1993 |
| FR | 2 674 126 | 9/1992 | WO | WO 94/18261 | 8/1994 |
| FR | 2 785 179 | 5/2000 | WO | WO 94/21233 | 9/1994 |
| FR | 2 796 270 | 1/2001 | WO | WO 95/15741 | 6/1995 |
| FR | 2 796 271 | 1/2001 | WO | WO 95/24887 | 9/1995 |
| FR | 2 796 272 | 1/2001 | WO | WO 95/33000 | 12/1995 |
| FR | 2 796 273 | 1/2001 | WO | WO 96/15761 | 5/1996 |
| FR | 2 796 276 | 1/2001 | WO | WO 96/40044 | 12/1996 |
| FR | 2 796 550 | 1/2001 | WO | WO 97/17057 | 5/1997 |
| FR | 2 802 806 | 6/2001 | WO | WO 97/36573 | 10/1997 |
| FR | 2 804 014 | 7/2001 | WO | WO 98/17243 | 4/1998 |
| FR | 2 804 017 | 7/2001 | WO | WO 98/17705 | 4/1998 |
| FR | 2 804 018 | 7/2001 | WO | WO 98/22078 | 5/1998 |
| FR | 2 810 562 | 12/2001 | WO | WO 98/25922 | 6/1998 |
| FR | 2 811 225 | 1/2002 | WO | WO 98/27162 | 6/1998 |

| WO | WO 98/42298 | 10/1998 |
| WO | WO 98/47470 | 10/1998 |
| WO | WO 98/52534 | 11/1998 |
| WO | WO 98/58623 | 12/1998 |
| WO | WO 99/24002 | 5/1999 |
| WO | WO 00/27350 | 5/2000 |
| WO | WO 00/40216 | 7/2000 |
| WO | WO 00/61080 | 10/2000 |
| WO | WO 00/61081 | 10/2000 |
| WO | WO 00/74519 A2 | 12/2000 |
| WO | WO 01/51020 | 7/2001 |
| WO | WO 01/52799 A1 | 7/2001 |
| WO | WO 01/97758 A2 | 12/2001 |
| WO | WO 01/97773 A1 | 12/2001 |
| WO | WO 02/03932 A2 | 1/2002 |
| WO | WO 02/03935 A2 | 1/2002 |
| WO | WO 02/03950 A2 | 1/2002 |
| WO | WO 02/03951 A2 | 1/2002 |
| WO | WO 02/47605 A2 | 6/2002 |
| WO | WO 02/47606 A2 | 6/2002 |
| WO | WO 02/47608 A2 | 6/2002 |
| WO | WO 02/47619 A2 | 6/2002 |
| WO | WO 02/47620 | 6/2002 |
| WO | WO 02/47622 A2 | 6/2002 |
| WO | WO 02/47627 A1 | 6/2002 |
| WO | WO 02/47629 A1 | 6/2002 |
| WO | WO 02/47630 A1 | 6/2002 |
| WO | WO 02/47658 | 6/2002 |
| WO | WO 02/49583 A1 | 6/2002 |
| WO | WO 02/49601 | 6/2002 |
| WO | WO 02/055030 A2 | 7/2002 |
| WO | WO 02/055031 A1 | 7/2002 |
| WO | WO 02/056845 A1 | 7/2002 |
| WO | WO 02/056847 A1 | 7/2002 |
| WO | WO 02/056848 A1 | 7/2002 |
| WO | WO 02/092047 A1 | 11/2002 |
| WO | WO 02/092663 A1 | 11/2002 |
| WO | WO 02/102322 A2 | 12/2002 |
| WO | WO 2005/013887 A2 | 2/2005 |

OTHER PUBLICATIONS

English language Derwent abstract of JP 02/200612.
English language Derwent abstract of JP 09/255560.
English language Derwent abstract of JP 10/007527.
English language Derwent abstract of EP 0 820 764 A1.
English language Derwent abstract of JP 10/212213.
English language Derwent abstract of EP 0 923 928 A1.
English language Derwent abstract of EP 0 925 780 A1.
English language Derwent abstract of EP 0 943 340 A1.
English language Derwent abstract of EP 1 068 856 A1.
English language Derwent abstract of FR 2 796 270.
English language Derwent abstract of FR 2 796 271.
English language Derwent abstract of FR 2 796 276.
English language Derwent abstract of FR 2 811 552 A1.
English language Derwent abstract of FR 2 816 506.
Milan Jokić et al., *A Novel Type of Small Organic Gelators: Bis(Amino Acid) Oxalyl Amides*, 1995 J. Chem. Soc., Chem. Commun., 1723.
Kenji Hanabusa et al., *Prominent Gelation and Chiral Aggregation of Alkylamides Derived from trans-1,2-Diaminocyclohexane*, Angew. Chem. Int. Ed. Engl. 1996, 35, No. 17, 1949-1951.
Toshimi Shimizu et al., *Stereochemical Effect of Even-Odd Connecting Links on Supramolecular Assemblies Made of 1-Glucosamide Bolaamphiphiles*, J. Am Chem. Soc. 1997, 119, 2812-2818.
P. Terech, "Low-Molecular Weight Organogelators," in *Specialist Surfactants*, ch. 8, pp. 208-268 (I.D. Robb, ed., 1997).
Kenji Hanabusa et al., *Terephyhaloyl Derivatives as New Gelators; Excellent Gelation Ability and Remarkable Increase of Gel Strength by Adding Polymers*, 1999 Chemistry Letters 767.
Xuzhong Luo et al., *Self-assembled organogels formed by monoalkyl derivatives of oxamide*, 2000 Chem. Commun. 2091-92.
Kenji Hanabusa et al., *Easy Preparation and Gelation of New Gelator Based on L-Lysine*, 2000 Chem. Letters, 1070.
International Search Report in PCT/US 01/47499, dated Aug. 8, 2002.
International Search Report in PCT/US 01/47454, dated Aug. 29, 2002.
1993 McCutcheon's vol. 1: Emulsifiers & Detergents North American and International Editions, MC Publishing Co., Glen Rock NJ (1993), pp. 272-273.
Bush Boake Allen, Inc., Uniclear Formulations, dated Oct. 13, 1998.
Certified English translation of FR 1 529 329.
Charles M. Hansen, "The Three Dimensional Solubility Parameter—Key to Paint Component Affinities: I. Solvents, Plasticizers, Polymers, and Resins," Journal of Paint Technology, vol. 39, No. 505, Feb. 1967, pp. 104-117.
Co-Pending U.S. Appl. No. 09/618,066; Title: Compositions in Rigid Form Structured With a Polymer Inventors: Véronique Ferrari and Pascal Simon, filed Jul. 17, 2000.
Co-Pending Appl. No. 09/685,577; Title: Compositions in Rigid Form Structured With a Polymer Inventors: Véronique Ferrari and Pascal Simon, filed Oct. 11, 2000.
Co-Pending U.S. Appl. No. 09/685,578; Title: Composition Containing a Liquid Fatty Phase Gelled With a Polyamide Containing Ester End Groups Inventor: Véronique Ferrari, filed Oct. 11, 2000.
Co-Pending U.S. Appl. No. 09/733,896; Title: Compositions Containing Heteropolymers and Oil-Soluble Polymers and Methods of Using Same Inventors: Carlos Pinzon and Paul Thau, filed Dec. 12, 2000.
Co-Pending U.S. Appl. No. 09/733,897; Title: Compositions Containing Heteropolymers and Methods of Using Same Inventors: Carlos Pinzon and Paul Thau, filed Dec. 12, 2000.
Co-Pending U.S. Appl. No. 09/733,898; Title: Compositions Containing Heteropolymers and Oil-Soluble Esters and Methods of Using Same Inventors: Carlos Pinzon and Paul Thau, filed Dec. 12, 2000.
Co-Pending U.S. Appl. No. 09/733,899; Title: Cosmetic Compositions Containing at Least One Hetero Polymer and at Least One Film-Forming Silicone Resin and Methods of Using Inventors: Mohamed Kanji et al., filed Dec. 12, 2000.
Co-Pending U.S. Appl. No. 09/733,900; Title: Cosmetic Compositions Containing Heteropolymers and Oil-Soluble Cationic Surfactants and Methods of Using Inventors: Carlos Pinzon and Paul Thau, filed Dec. 12, 2000.
Co-Pending U.S. Appl. No. 09/749,036; Title: Composition Comprising at Least One Hetero Polymer and at Least One Pasty Fatty Substance and Methods for Use Inventors: Véronique Ferrari et al., filed Dec. 28, 2000.
Co-Pending U.S. Appl. No. 09/937,314; Title: Transfer-Free Composition Structured in the Stiff Form by a Polymer, filed Sep. 24, 2001.
Co-Pending U.S. Appl. No. 10/012,029; Title: Cosmetic Composition Comprising a Polymer Blend, filed Dec. 11, 2001.
Co-Pending U.S. Appl. No. 10/012,051; Title: Use of a Polymer for Obtaining an Express Make-Up of Keratin Materials, filed Dec. 11, 2001.
Co-Pending U.S. Appl. No. 10/012,052; Title: Cosmetic Composition Comprising a Wax and a Polymer, filed Dec. 11, 2001.
Co-Pending U.S. Appl. No. 10/046,568; Title: Nail Polish Composition Comprising a Polymer, filed Jan. 16, 2002.
Co-Pending U.S. Appl. No. 10/047,987, Title: Cosmetic Composition Containing a Polymer and a Fluoro Oil, filed Jan. 17, 2002.
Co-Pending U.S. Appl. No. 10/129,377; Title: Compositions Structured With a Polymer Containing a Heteroatom and an Organogelator, filed May 3, 2002.
Co-Pending U.S. Appl. No. 10/198,931, Title: Compositions Comprising at Least One Heteropolymer and Fibers, and Methods of Using the Same, filed Jul. 22, 2002.
Co-Pending U.S. Appl. No. 10/203,018; Title: Composition Comprising at Least One Hetero Polymer and at Least One Inert Filler and Methods for Use, filed Aug. 5, 2002.
Co-Pending U.S. Appl. No. 10/203,254; Title: Cosmetic Compositions Containing at Least One Heteropolymer and at Least One Gelling Agent and Methods of Using the Same, filed Aug. 7, 2002.

Co-Pending U.S. Appl. No. 10/203,374, Title: Method for Making a Coloured Make-Up Cosmetic Composition With Controlled Transmittance, filed Aug. 9, 2002.
Co-Pending U.S. Appl. No. 10/203,375, Title: Transparent or Translucent Colored Cosmetic Composition, filed Aug. 9, 2002.
Co-Pending U.S. Appl. No. 10/312,083, Title: Solid Emulsion Containing a Liquid Fatty Phase Structured With a Polymer, filed Dec. 23, 2002.
Co-Pending U.S. Appl. No. 10/413,217, Title: Methods of Dispersing at Least One Coloring Agent Using at Least One Heteropolymer, filed Apr. 15, 2003.
Co-Pending U.S. Appl. No. 10/450,108, Title: Cosmetic Composition Comprising a Polymer and Fibres, filed Jun. 11, 2003.
Co-Pending U.S. Appl. No. 10/459,636, Title: Cosmetic Emulsions Containing at Least One Hetero Polymer and at Least One Sunscreen and Methods of Using the Same, filed Jun. 12, 2003.
Co-Pending U.S. Appl. No. 10/466,166, Title: Cosmetic Composition Comprising a Mixture of Polymers, filed Jul. 14, 2003.
Co-Pending U.S. Appl. No. 10/618,315, Title: Cosmetic Compositions Comprising a Structuring Agent, Silicone Powder and Swelling Agent, filed Jul. 11, 2003.
Co-Pending U.S. Appl. No. 10/699,780, Title: Methods of Dispersing at Least One Coloring Agent Using at Least One Heteropolymer, filed Nov. 4, 2003.
Co-Pending U.S. Appl. No. 10/746,612, Title: Cosmetic Compositions Comprising a Structuring Agent, Silicone Powder and Swelling Agent, filed Dec. 22, 2003.
Co-Pending U.S. Appl. No. 10/747,412, Title: Cosmetic Emulsions Containing at Least One Hetero Polymer and at Least One Sunscreen and Methods of Using the Same, filed Dec. 22, 2003.
Co-Pending U.S. Appl. No. 10/787,440, Title: Compostition Comprising at Least One Hetero Polymer and at Least One Inert Filler and Methods for Use, filed Feb. 27, 2004.
Co-Pending U.S. Appl. No. 10/787,441; Title: Cosmetic Composition Comprising Hetero Polymers and a Solid Substance and Method of Using Same, filed Feb. 27, 2004.
Co-Pending U.S. Appl. No. 10/918,579, Title: Compositions Containing Heteropolymers and OilSoluble Esters and Methods of Using Same, filed Aug. 16, 2004.
Co-Pending Application No. Not Yet Assigned, Title: Cosmetic Composition Comprising a Polymer Blend, filed Nov. 22, 2004.
Co-Pending Application No. Not Yet Assigned, Title: A Transfer-Free Composition Structured in Rigid Form by a Polymer, filed Nov. 22, 2004.
Co-Pending Application No. Not Yet Assigned, Title: Use of a Polymer for Obtaining an Express Make-Up of Keratin Materials, filed Nov. 18, 2004.
English language abstract of JP 53/043577 from Patent Abstracts of Japan.
English language abstract of JP 56/123909 from Patent Abstracts of Japan.
English language abstract of JP 56/166276 from Patent Abstracts of Japan.
English language Derwent abstract of JP 78/043577.
English language Derwent abstract of DE 195 43 988 A1.
English language Derwent abstract of DE 197 07 309 A1.
English language Derwent abstract of DE 197 50 246 A1.
English language Derwent abstract of DE 199 51 010 A1.
English language Derwent abstract of DE 38 39 136 A.
English language Derwent abstract of DE 38 43 892 A1.
English language Derwent abstract of DE 42 08 297 A1.
English language Derwent abstract of DE 42 34 886 A1.
English language Derwent abstract of EP 0 169 997 B.
English language Derwent abstract of EP 0 557 196 A1.
English language Derwent abstract of EP 0 609 132 B1.
English language Derwent abstract of EP 0 749 746 A1.
English language Derwent abstract of EP 0 749 747 A1.
English language Derwent abstract of EP 0 749 748 A1.
English language Derwent abstract of EP 0 775 483 A1.
English language Derwent abstract of EP 0 847 752 A1.
English language Derwent abstract of EP 0 879 592 A2.
English language Derwent abstract of EP 0 887 073 A1.
English language Derwent abstract of EP 0 930 058 B1.
English language Derwent abstract of EP 0 930 060 A1.
English language Derwent abstract of EP 0 958 811 A1.
English language Derwent abstract of EP 0 959 066 A2.
English language Derwent abstract of EP 0 959 091 A1.
English language Derwent abstract of EP 0 976 390 A1.
English language Derwent abstract of EP 1 002 514 A1.
English language Derwent abstract of EP 1 031 342 A1.
English language Derwent abstract of EP 1 048 282 A1.
English language Derwent abstract of EP 1 053 742 A1.
English language Derwent abstract of EP 1 064 919 A1.
English language Derwent abstract of EP 1 064 920 A1.
English language Derwent abstract of EP 1 066 814 A1.
English language Derwent abstract of EP 1 068 854 A1.
English language Derwent abstract of EP 1 068 855 A1.
English language Derwent abstract of EP 1 086 945 A1.
English language Derwent abstract of EP 1 090 627 A1.
English language Derwent abstract of EP 1 114 636 A1.
English language Derwent abstract of FR 2 232 303.
English language Derwent abstract of FR 2 674 126.
English language Derwent abstract of FR 2 785 179.
English language Derwent abstract of FR 2 796 272.
English language Derwent abstract of FR 2 796 273.
English language Derwent abstract of FR 2 802 806.
English language Derwent abstract of FR 2 804 017.
English language Derwent abstract of FR 2 804 018.
English language Derwent abstract of FR 2 810 562.
English language Derwent abstract of FR 2 811 225.
English language Derwent abstract of FR 2 817 739.
English language Derwent abstract of FR 2 817 740.
English language Derwent abstract of FR 2 817 743.
English language Derwent abstract of FR 2 819 399.
English language Derwent abstract of FR 2 819 400.
English language Derwent abstract of FR 2 819 402.
English language Derwent abstract of JP 04/346909.
English language Derwent abstract of JP 10/120903.
English language Derwent abstract of JP 10/259344.
English language Derwent abstract of JP 11/106216.
English language Derwent abstract of JP 11/335228.
English language Derwent abstract of JP 11/335242.
English language Derwent abstract of JP 11/335254.
English language Derwent abstract of JP 2/127568.
English language Derwent abstract of JP 2000038314 A.
English language Derwent abstract of JP 2000038316 A and JP 2000038317 A.
English language Derwent abstract of JP 2000038321 A.
English language Derwent abstract of JP 2000086427 A.
English language Derwent abstract of JP 2000086429 A.
English language Derwent abstract of JP 2000086438 A.
English language Derwent abstract of JP 2/216279.
English language Derwent abstract of JP 3/014683.
English language Derwent abstract of JP 61/065809.
English language Derwent abstract of JP 7/179795.
English language Derwent abstract of JP 7/267827.
English language Derwent abstract of JP 8/225316.
English language Derwent abstract of JP 9/20631.
English language Derwent abstract of JP 9/295922.
English language Derwent abstract of WO 01/97773.
English language Derwent abstract of WO 02/056847.
English language Derwent abstract of WO 02/056848.
English language Derwent abstract of WO 02/47622.
English language Derwent abstract of WO 02/47629.
English language Derwent abstract of WO 02/47630.
English language Derwent abstract of WO 86/04916.
Estee Lauder MagnaScopic Maximum Volume mascara product packaging, believed to have first been sold in 2003.
French Search Report in FR 0000920, dated Nov. 10, 2000.
French Search Report in FR 0001004, dated Nov. 10, 2000.
French Search Report in FR 0008084, dated Mar. 28, 2001.
French Search Report in FR 0008913, dated Mar. 20, 2001.
French Report Report in FR 0016161, dated Sep. 6, 2001.
French Search Report in FR 0016163, dated Aug. 1, 2001.
French Search Report in FR 0016164, dated Sep. 6, 2001.
French Search Report in FR 0016180, dated Oct. 16, 2001.

French Search Report in FR 0100479, dated Sep. 17, 2001.
French Search Report in FR 0100620, dated Nov. 6, 2001.
French Search Report in FR 0100623, dated Oct. 9, 2001.
French Search Report in FR 0114529, dated Aug. 26, 2002.
French Search Report in FR 0114530, dated Aug. 26, 2002.
French Search Report in FR 9909176, dated Mar. 23, 2000.
French Search Report in FR 9909177, dated Mar. 30, 2000.
French Search Report in FR 9916588, dated Oct. 16, 2000.
Handbook of Cosmetic Science and Tech. Elsevier Advanced Tech., 1st Edition (1994), pp. 1-32.
International Search Report in PCT/FR01/00229, dated Apr. 18, 2001.
International Search Report in PCT/FR01/01958, dated Oct. 26, 2001.
International Search Report in PCT/FR01/03726, dated Apr. 18, 2002.
International Search Report in PCT/FR01/03937, dated Apr. 23, 2002.
International Search Report in PCT/FR01/03938, dated Jun. 10, 2002.
International Search Report in PCT/FR01/03939, dated Apr. 15, 2002.
International Search Report in PCT/FR01/03940, dated Mar. 13, 2002.
International Search Report in PCT/FR01/03945, dated May 31, 2002.
International Search Report in PCT/FR02/00129, dated Jun. 14, 2002.
International Search Report in PCT/FR02/00144, dated Jun. 14, 2002.
International Search Report in PCT/FR02/00194, dated Jun. 12, 2002.
International Search Report in PCT/IB00/02000, dated Aug. 8, 2001.
International Search Report in PCT/IB00/02002, dated Sep. 4, 2001.
International Search Report in PCT/IB00/02006, dated Aug. 8, 2001.
International Search Report in PCT/IB01/02780, dated Oct. 4, 2002.
International Search Report in PCT/IB01/02786, dated Oct. 2, 2002.
International Search Report in PCT/IB01/02820, dated May 27, 2002.
International Search Report in PCT/IB01/02833, dated May 24, 2002.
International Search Report in PCT/IB01/02840, dated Jun. 11, 2002.
International Search Report in PCT/US 00/33596, dated Aug. 8, 2001.
International Search Report in PCT/US 01/47459, dated Feb. 6, 2003.
International Search Report in PCT/US 01/47496, dated Feb. 26, 2003.
International Search Report in PCT/US 01/47497, dated Dec. 2, 2002.
Kirk-Othmer, "Encyclopedia of Chemical Technology", Third Edition, vol. 22, John Wiley & Sons, 1983, pp. 332-342.
Office Action in co-pending U.S. Appl. No. 09/618,066 dated Dec. 21, 2001.
Office Action in co-pending U.S. Appl. No. 09/618,066 dated Jul. 15, 2002.
Office Action in co-pending U.S. Appl. No. 09/618,066 dated Jul. 16, 2003.
Office Action in co-pending U.S. Appl. No. 09/618,066 dated Nov. 19, 2003.
Office Action in co-pending U.S. Appl. No. 09/685,577 dated Aug. 11, 2004.
Office Action in co-pending U.S. Appl. No. 09/685,577 dated Jul. 15, 2002.
Office Action in co-pending U.S. Appl. No. 09/685,577 dated Jul. 16, 2003.
Office Action in co-pending U.S. Appl. No. 09/685,577 dated Nov. 19, 2003.
Office Action in co-pending U.S. Appl. No. 09/685,578 dated Aug. 11, 2004.
Office Action in co-pending U.S. Appl. No. 09/685,578 dated May 7, 2003.
Office Action in co-pending U.S. Appl. No. 09/685,578 dated Nov. 19, 2003.
Office Action in co-pending U.S. Appl. No. 09/733,896 dated Jan. 28, 2003.
Office Action in co-pending U.S. Appl. No. 09/733,896 dated Jul. 19, 2002.
Office Action in co-pending U.S. Appl. No. 09/733,896 dated Nov. 18, 2003.
Office Action in co-pending U.S. Appl. No. 09/733,897 dated Apr. 15, 2002.
Office Action in co-pending U.S. Appl. No. 09/733,897 dated Apr. 23, 2003.
Office Action in co-pending U.S. Appl. No. 09/733,897 dated Aug. 29, 2002.
Office Action in co-pending U.S. Appl. No. 09/733,897 dated May 6, 2004.
Office Action in co-pending U.S. Appl. No. 09/733,898 dated Apr. 29, 2003.
Office Action in co-pending U.S. Appl. No. 09/733,898 dated Aug. 28, 2002.
Office Action in co-pending U.S. Appl. No. 09/733,898 dated Dec. 23, 2003.
Office Action in co-pending U.S. Appl. No. 09/733,899 dated Apr. 7, 2004.
Office Action in co-pending U.S. Appl. No. 09/733,899 dated Apr. 9, 2003.
Office Action in co-pending U.S. Appl. No. 09/733,899 dated Sep. 22, 2004.
Office Action in co-pending U.S. Appl. No. 09/733,900 dated Apr. 7, 2004.
Office Action in co-pending U.S. Appl. No. 09/733,900 dated Jul. 16, 2003.
Office Action in co-pending U.S. Appl. No. 09/749,036 dated Aug. 13, 2003.
Office Action in co-pending U.S. Appl. No. 09/749,036 dated Jul. 16, 2002.
Office Action in co-pending U.S. Appl. No. 09/749,036 dated May 5, 2004.
Office Action in co-pending U.S. Appl. No. 09/899,909 dated Dec. 18, 2001.
Office Action in co-pending U.S. Appl. No. 09/937,314 dated May 19, 2004.
Office Action in co-pending U.S. Appl. No. 09/971,028 dated Aug. 11, 2003.
Office Action in co-pending U.S. Appl. No. 09/971,028 dated Mar. 26, 2003.
Office Action in co-pending U.S. Appl. No. 10/012,029 dated Nov. 20, 2002.
Office Action in co-pending U.S. Appl. No. 10/012,029 dated Sep. 8, 2003.
Office Action in co-pending U.S. Appl. No. 10/012,051 dated Jan. 14, 2003.
Office Action in co-pending U.S. Appl. No. 10/012,051 dated May 14, 2004.
Office Action in co-pending U.S. Appl. No. 10/012,051 dated Oct. 3, 2003.
Office Action in co-pending U.S. Appl. No. 10/012,052 dated Nov. 6, 2003.
Office Action in co-pending U.S. Appl. No. 10/012,052 dated Aug. 9, 2004.
Office Action in co-pending U.S. Appl. No. 10/046,568 dated Dec. 30, 2003.
Office Action in co-pending U.S. Appl. No. 10/046,568 dated Jun. 12, 2003.
Office Action in co-pending U.S. Appl. No. 10/046,568 dated Nov. 5, 2002.
Office Action in co-pending U.S. Appl. No. 10/046,568 dated Sep. 22, 2004.
Office Action in co-pending U.S. Appl. No. 10/047,987 dated Dec. 11, 2003.
Office Action in co-pending U.S. Appl. No. 10/047,987 dated Sep. 7, 2004.
Office Action in co-pending U.S. Appl. No. 10/182,830 dated Aug. 24, 2004.

Office Action in co-pending U.S. Appl. No. 10/198,931 dated Dec. 18, 2003.
Office Action in co-pending U.S. Appl. No. 10/198,931 dated Sep. 1, 2004.
Office Action in co-pending U.S. Appl. No. 10/203,018 dated May 19, 2004.
Office Action in co-pending U.S. Appl. No. 10/312,083 dated Oct. 1, 2004.
Office Action in co-pending U.S. Appl. No. 10/413,217 dated Sep. 9, 2004.
Office Action in co-pending U.S. Appl. No. 10/699,780 dated Sep. 22, 2004.
Office Action in co-pending U.S. Appl. No. 10/746,612 dated Sep. 20, 2004.
Office Action in co-pending U.S. Appl. No. 10/787,440 dated Aug. 24, 2004.
Origins Full StoryTM Lush lash mascara product packaging, believed to have first been sold in 2003.
Partial International Search Report in PCT/US 01/47497, dated Nov. 15, 2002.
PCT Application No. PCT/FR01/03962; Title: Composition Comprising at Least One Heteropolymer and at Least One Inert Filler and Methods for Use Inventors: Véronique Ferrari et al. International Filing Date: Dec. 12, 2001.
PCT Application No. PCT/FR01/03963; Title: Cosmetic Compositions Containing at Least One Heteropolymer and at Least One Gelling Agent and Methods of Using the Same Inventor: Véronique Ferrari International Filing Date: Dec. 12, 2001.
PCT Application No. PCT/FR01/03965; Title Cosmetic Composition Comprising Hetero Polymers and a Solid Substance and Method of Using Same Inventors: Roberto Cavazzuti et al. International Filing Date: Dec. 12, 2001.
PCT Application No. PCT/IB00/02000; Title: Composition Comprising at Least One Hetero Polymer and at Least One Inert Filler and Methods for Use Inventors: Véronique Ferrari et al. International Filing Date: Dec. 12, 2000.
PCT Application No. PCT/IB00/02006; Title: Cosmetic Composition Containing at Least One Heteropolymer and at Least One Gelling Agent and Methods of Using the Same Inventor: Véronique Ferrari International Filing Date:Dec. 12, 2000.
PCT Application No. PCT/IB01/02780; Title:Composition Structured With a Polymer Containing a Heteroatom Organogelator International Filing Date: Dec. 12, 2001.
PCT Application No. PCT/US00/33596; Title Cosmetic Composition Comprising Hetero Polymers and a Solid Substance and Method of Using Same Inventors: Roberto Cavazzuti et al. International Filing Date: Dec. 12, 2000.
PCT Application No. PCT/US01/47454; Title: Compositions Containing Heteropolymers and Oil-Soluble Polymers and Methods of Using Same Inventors: Carlos Pinzon and Paul Thau U.S. Filing Date: Dec. 12, 2001.
PCT Application No. PCT/US01/47459; Title: Cosmetic Compositions Containing at Least One Hetero Polymer and at Least One Film-Forming Silicone Resin and Methods of Using Inventors: Mohamed Kanji et al. U.S. Filing Date:Dec. 12, 2001.
PCT Application No. PCT/US01/47496; Title: Compositions Containing Heteropolymers and Methods of Using Same Inventors: Carlos Pinzon and Paul Thau U.S. Filing Date: Dec. 12, 2001.
PCT Application No. PCT/US01/47497; Title: Compositions Containing Heteropolymers and Oil-Soluble Esters and Methods of Using Same Inventors: Carlos Pinzon and Paul Thau U.S. Filing Date: Dec. 12, 2001.
PCT Application No. PCT/US01/47499; Title: Cosmetic Compositions Containing Heteropolymers and Oil-Soluble Cationic Surfactants and Methods of Using Same Inventors: Carlos Pinzon and Paul Thau U.S. Filing Date: Dec. 12, 2001.
PCT Application No. PCT/US03/41618; Title: Cosmetic Compositions Comprising a Structuring Agent, Silicone Powder and Swelling Agent Inventors: Shao Xiang Lu , Terry Van Liew, Nathalie Geffroy-Hyland International Filing Date: Dec. 22, 2003.
PCT Application No. PCT/US04/01071; Title: Long Wear Cosmetic Composition Inventor: Balanda ATIS International Filing Date: Jan. 16, 2004.

Toshimi Shimizu et al., Stereochemical Effect of Even-Odd Connecting Links on Supramolecular Assemblies Made of 1-Glucosamide Bolaamphiphiles, J. Am Chem. Soc. 1997, 119, 2812-2818.
Yasuda et al., Novel Low-molecular-weight Organic Gels: N,N', N"-Tristearyltrimesamide/Organic Solvent System, Chemistry Letters, pp. 575-576, 1996, the month of publication is not available.
Bangham, A.D. et al. Diffusion of Univalent Ions across the Lamellae of Swollen Phospholids, Journal of Molecular Biology, pp. 238-252, vol. 13, Aug. to Oct. 1965.
Co-Pending U.S. Appl. No. 10/494,864; Title: Composition Containing an Amino Acid-N-Acylated Ester and a Polyamide-Structured UV Filter, filed Nov. 23, 2004.
Co-Pending U.S. Appl. No. 11/019,382, Title: Cosmetic Composition Comprising Two Different Hetero Polymers and Method of Using Same, filed Dec. 23, 2004.
English Language Abstract of FR 2 804 014 from esp@cenet.
English Language Abstract of FR 2 817 742 from esp@cenet.
English language abstract of JP 02/207014 from Patent Abstracts of Japan.
English language Derwent abstract of DE 197 26 184.
English language Derwent abstract of DE 197 55 649 A1.
English language Derwent abstract of DE 198 55 649 A1.
English language Derwent abstract of EP 0 507 692 A1.
English language Derwent abstract of EP 0 518 772 A1.
English language Derwent abstract of EP 0 518 773 A1.
English language Derwent abstract of EP 0 669 323 A1.
English language Derwent abstract of EP 0 775 698 A1.
English language Derwent abstract of EP 0 790 243 A1.
English language Derwent abstract of EP 0 863 145 A2.
English language Derwent abstract of EP 0 878 469 A1.
English language Derwent abstract of EP 0 967 200 A1.
English language Derwent abstract of FR 2 315 991.
English language Derwent abstract of FR 2 416 008.
English language Derwent abstract of FR 2 796 550.
English language Derwent abstract of WO 93/04665.
English language Derwent abstract of WO 98/25922.
Harry's Cosmeticology 375-383 (J.B. Wilkinson & R.J. Moore eds., Chemical Pub. 7th ed. 1982).
International Search Report in PCT/US03/41618, dated Mar. 11, 2005.
International Search Report in PCT/US04/01071, dated Feb. 22, 2005.
McCutcheon's vol. 1: Emulsifiers & Detergents, North American Edition MC Publishing Co., Glen Rock NJ (1993), pp. 272-273.
Richard J. Lewis, Sr., "Ricinoleic Acid," Hawley's Condensed Chemical Dictionary 972 (13th. 1997).
Co-Pending U.S. Appl. No. 11/212,811, Title: A Transfer-Free Mascara Composition Comprising at Least One Volatile Solvent and at Least One Polymer, filed Aug. 29, 2005.
Co-Pending U.S. Appl. No. 11/351,309, Title: Cosmetic Composition Containing a Polymer and a Fluoro Oil, filed Feb. 6, 2006.
Co-Pending U.S. Appl. No. 11/312,338, Title: Composition and Process for Coating Keratin Fibers, filed Dec. 21, 2005.
Office Action in co-pending U.S. Appl. No. 10/129,377 dated Jan. 13, 2006.
Office Action in co-pending U.S. Appl. No. 09/749,036 dated Nov. 23, 2005.
Office Action in co-pending U.S. Appl. No. 10/203,254 dated Dec. 5, 2005.
Office Action in co-pending U.S. Appl. No. 10/312,083 dated Sep. 28, 2005.
Office Action in co-pending U.S. Appl. No. 10/990,475 dated Nov. 2, 2005.
Office Action in co-pending U.S. Appl. No. 11/212,811 dated Nov. 17, 2005.
Office Action in co-pending U.S. Appl. No. 09/733,896 dated Jan. 30, 2006.
Estee Lauder's Amended Answer and Counterclaims, dated Apr. 21, 2005, in the on-going litigation *L'Oreal S.A., et al., v. The Estee Lauder Companies Inc., et al.,* Civil Action No. 04-1660 (D.N.J.).

Estee Lauder's Response to Plaintiff's First Set of Interrogatories (Nos. 1-6), dated Sep. 27, 2004, in the on-going litigation *L'Oreal S.A., et al.* v. *The Estee Lauder Companies Inc., et al.*, Civil Action No. 04-1660 (D.N.J.).

Estee Lauder's Response to Plaintiff's Third Set of Interrogatories (Nos. 8-13), dated Jun. 21, 2005, in the on-going litigation *L'Oreal S.A., et al.* v. *The Estee Lauder Companies Inc., et al.*, Civil Action No. 04-1660 (D.N.J.).

U.S. District Court for the District of New Jersey Civil Docket for *L'Oreal S.A. et al.* v. *Estee Lauder Companies, Inc., et al.*, Civ. No. 04-1660 (HAA) (filed Apr. 7, 2004) (retrieved Jan. 2, 2005).

Bangham, A.D. et al. Diffusion of Univalent Ions across the Larnellae of Swollen Phospholipids, Journal of Molecular Biology, pp. 238-252, vol. 13, Aug. to Oct. 1965.

Co-Pending U.S. Appl. 11/019,382, Title: Cosmetic Composition Comprising Two Different Hetero Polymers and Method of Using Same, filed Dec. 23, 2004.

English Language Abstract of FR 2 804 014 from esp@cenet.

English Language Abstract of FR 2 817 742 from esp@cenet.

English language abstract of JP 02/207014 from Patent Abstracts of Japan.

English language Derwent abstract of DE 197 26 184.

English language Derwent abstract of DE 197 55 649 A1.

English language Derwent abstract of DE 198 55 649 A1.

English language Derwent abstract of EP 0 507 692 A1.

English language Derwent abstract of EP 0 518 772 A1.

English language Derwent abstract of EP 0 518 773 A1.

English language Derwent abstract of EP 0 669 323 A1.

English language Derwent abstract of EP 0 775 698 A1.

English language Derwent abstract of EP 0 790 243 A1.

English language Derwent abstract of EP 0 863 145 A2.

English language Derwent abstract of EP 0 878 469 A1.

English language Derwent abstract of EP 0 967 200 A1.

English language Derwent abstract of FR 2 315 991.

English language Derwent abstract of FR 2 416 008.

English language Derwent abstract of FR 2 796 550.

English language Derwent abstract of WO 93/04665.

English language Derwent abstract of WO 98/25922.

Estee Lauder's Amended Answer and Counterclaims, dated Apr. 21, 2005, in the on-going litigation *L'Oreal S.A., et al.*, v. *The Estee Lauder Companies Inc., et al.*, Civil Action No. 04-1660 (D.N.J.).

Estee Lauder's Response to Plaintiff's First Set of Interrogatories (Nos. 1-6), dated Sep. 27, 2004, in the on-going litigation *L'Oreal S.A., et al.* v. *The Estee Lauder Companies Inc., et al.*, Civil Action No. 04-1660 (D.N.J.).

Estee Lauder's Response to Plaintiff's Third Set of Interrogatories (Nos. 8-13), dated Jun. 21, 2005, in the on-going litigation *L'Oreal S.A., et al.* v. *The Estee Lauder Companies Inc., et al.*, Civil Action No. 04-1660 (D.N.J.).

Harry's Cosmeticology 375-383 (J.B. Wilkinson & R.J. Moore eds., Chemical Pub. 7th ed. 1982).

International Search Report in PCT/US03/41618, dated Mar. 11, 2005.

International Search Report in PCT/US04/01071, dated Feb. 22, 2005.

McCutcheon's vol. 1: Emulsifiers & Detergents, North American Edition MC Publishing Co., Glen Rock NJ (1993), pp. 272-273.

Office Action in co-pending U.S. Appl. No. 09/685,578 dated Feb. 8 2005.

Office Action in co-pending U.S. Appl. No. 09/733,896 dated Jul. 13, 2005.

Office Action in co-pending U.S. Appl. No. 09/733,898 dated Apr. 25, 2005.

Office Action in co-pending U.S. Appl. No. 09/733,899 dated May 3, 2005.

Office Action in co-pending U.S. Appl. No. 09/733,900 dated Dec. 1, 2004.

Office Action in co-pending U.S. Appl. No. 09/733,900, dated Jun. 2, 2005.

Office Action in co-pending U.S. Appl. No. 09/749,036 dated Apr. 29, 2005.

Office Action in co-pending U.S. Appl. No. 10/012,052, dated Jun. 3, 2005.

Office Action in co-pending U.S. Appl. No. 10/182,830 dated Apr. 4, 2005.

Office Action in co-pending U.S. Appl. No. 10/203,254 dated Apr. 22, 2005.

Office Action in co-pending U.S. Appl. No. 10/203,375, dated May 13, 2005.

Office Action in co-pending U.S. Appl. No. 10/312,083 dated Apr. 18, 2005.

Office Action in co-pending U.S. Appl. No. 10/699,780, dated Jun. 15, 2005.

Office Action in co-pending U.S. Appl. No. 10/746,612 dated Jun. 15, 2005.

Office Action in co-pending U.S. Appl. No. 10/787,441, dated Apr. 5, 2005.

Richard J. Lewis, Sr., "Ricinoleic Acid," Hawley's Condensed Chemical Dictionary 972 (13th. 1997).

U.S. District Court for the District of New Jersey Civil Docket for *L'Oreal S.A. et al.* v. *Estee Lauder Companies, Inc., et al.*, Civ. No. 04-1660 (HAA) (filed Apr. 7, 2004) (retrieved Jan. 2, 2005).

\* cited by examiner

AT LEAST ONE POLYAMIDE POLYMER IN A COSMETIC COMPOSITION COMPRISING AT LEAST ONE SOLID SUBSTANCE HAVING A MELTING POINT OF 45 DEGREES C. OR GREATER

The present invention relates to compositions and methods for care of, for treating and for making-up for the skin, including the scalp, and/or for the lips, of human beings, and/or for other keratinous materials, such as keratinous fibers, comprising at least one liquid fatty phase structured with at least one structuring polymer containing a hetero atom. This invention may be in the form of a stable composition.

Structured liquid fatty phases in cosmetic or dermatological products are known in the art. As used herein, "structured" means gelled and/or rigidified. Structured liquid fatty phases may be found in solid compositions such as deodorants, balms, lip compositions, concealer products, and cast foundations.

As used herein, "liquid fatty phase" means a fatty phase which is liquid at room temperature (25° C.) and at atmospheric pressure (760 mmHg, i.e. 101 KPa) and which comprises at least one fatty substance, such as an oil, which is liquid at room temperature and not soluble in water. If the liquid fatty phase comprises two or more fatty substances, they should be mutually compatible, i.e. forming a homogeneous phase macroscopically.

Structured liquid fatty phases may make it possible to control the exudation of the liquid fatty phase from the solid compositions of which they are components, including exudation in a wet or hot atmosphere or environment. Structuring of the liquid fatty phase may also limit bleeding of this phase outside of the intended area of application and especially into wrinkles and fine lines after it has been deposited, for example, on keratinous material. As used herein, "keratinous material" is meant to comprise hair, lips, skin, scalp and superficial body growths such as eyelashes, eyebrows and nails. "Keratinous fiber" includes hair, eyelashes, and eyebrows. A large migration of a liquid fatty phase comprising coloring agents such as in lip or eyeshadow compositions may lead to an unaesthetic effect around the lips or eyes which may accentuate the wrinkles and fine lines. Consumers have cited this migration as a drawback of conventional lip and eyeshadow compositions.

U.S. Pat. No. 5,783,657, for example, describes structuring a composition by using a polyamide in a stick form. However, such a stick composition is usually not mechanically and/or thermally stable. Indeed, a part of the oil contained in such a composition tends to go outside or exude from the stick. Further, when the stick is applied on the skin or lips, said stick may be broken.

The inventors have found that the use of specific structuring polymers, defined more fully below, such as polyamide polymers, in at least one liquid fatty phase and the addition of a solid substance that has a melting point of about 45° C., for example about 47° C., or greater may make it possible to structure a composition comprising at least one liquid fatty phase while also resulting in a stable composition. As used herein, "about" before a number given as a melting point means the range or natural variation in the melting point. The range or variation may be due to impurities, crystallinity, and/or measurement method and conditions.

In one embodiment, the invention provides a composition comprising a liquid fatty phase which comprises: (i) at least one structuring polymer comprising a polymer skeleton which comprises at least one hydrocarbon-based repeating unit comprising at least one hetero atom; and (ii) at least one solid substance that has a melting point of about 45° C. or greater, wherein the at least one solid substance is not stearalkonium hectorite, silica, talc, or paraffin wax. In a further embodiment, the at least one solid substance that has a melting point of about 45° C. or greater is an organic solid substance.

As used herein, the expression "at least one" means one or more and thus includes individual components as well as mixtures/combinations.

In another embodiment, the invention provides a composition comprising a liquid fatty phase which comprises: (i) at least one structuring polymer, wherein said at least one structuring polymer is at least one polyamide polymer comprising a polymer skeleton which comprises at least one amide repeating unit; and (ii) at least one solid substance that has a melting point of 45° C. or greater, wherein the at least one solid substance is not stearalkonium hectorite, silica, talc, or paraffin wax. In further embodiment, the at least one solid substance that has a melting point of about 45° C. or greater is an organic solid substance.

In yet another embodiment, the invention provides an anhydrous composition comprising a liquid fatty phase which comprises: (i) at least one structuring polymer comprising a polymer skeleton which comprises at least one hydrocarbon-based repeating unit comprising at least one hetero atom; and (ii) at least one solid substance that has a melting point of about 45° C. or greater, wherein the at least one solid substance is not stearalkonium hectorite.

The invention also provides a composition comprising at least one liquid fatty phase which comprises: (i) at least one structuring polymer comprising a polymer skeleton which comprises at least one hydrocarbon-based repeating unit comprising at least one hetero atom; and at least one terminal fatty chain chosen from alkyl chains and alkenyl chains, wherein said at least one terminal fatty chain is bonded to said polymer skeleton via at least one linking group; and (ii) at least one solid substance that has a melting point of about 45° C. or greater.

In one embodiment, the at least one structuring polymer is present in an amount effective to provide structure to said fatty phase. The at least one structuring polymer and the at least one solid substance are present in a combined amount to provide the composition with stability. In a further embodiment, the at least one structuring polymer and the at least one solid substance provide resistance to shear. In a further embodiment, the at least one structuring polymer and the at least one solid substance provide the composition with stability and provide resistance to shear.

The invention also provides a method for providing stability to a composition comprising a liquid fatty phase, comprising: including in said liquid fatty phase at least one structuring polymer comprising a polymer skeleton which comprises at least one hydrocarbon-based repeating unit comprising at least one hetero atom, such as a structuring polymer comprising a polyamide skeleton. For example, the polymer skeleton comprises at least one end group with at least one chain chosen from alkyl chains comprising at least four carbon atoms and alkenyl chains comprising at least four carbon atoms, bonded to the at least one polyamide skeleton via at least one linking group. The polymer skeleton may comprise at least one terminal group and/or at least one pendant group with at least one chain chosen from alkyl chains comprising at least four carbon atoms and alkenyl chains comprising at least four carbon atoms, bonded to any carbon or nitrogen of the polyamide skeleton via at least one linking group. The at least one structuring polymer is present in an amount effective to provide structure to said fatty phase. At least one solid substance that has a melting point of about 45° C., for example about 47° C., or greater is also included in the composition. The components may be added in any order. The at least one structuring polymer and the at least one solid substance are present in a combined amount effective to provide the composition with stability.

It is to be understood that both the foregoing general description and the following detailed description are exemplary and explanatory only and are not restrictive of the invention as claimed.

One subject of the invention is cosmetic and/or dermatological compositions which are useful for the care, make-up and/or treating of at least one keratinous material, including at least one keratinous fiber, and nails which may be of suitable hardness to allow preparation of these compositions in the form of a stick or other structured form which may be stable.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as bending or leaning if the composition is in stick form, phase separation, melting, or syneresis. As used herein syneresis is the appearance of droplets on the surface of a composition that are visible to the naked eye. The stability is further tested by repeating the 8 week test at 4° C., 37° C., 45° C., 50° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

The invention applies not only to make-up products for at least one keratinous material such as lip compositions, lip pencils, foundations including foundations which may be cast in the form of a stick or a dish, concealer products, temporary tattoo products, eyeliners, mascara bars, but also to body hygiene products such as deodorant sticks, and to care products and products for treating at least one keratinous material, such as sunscreen and anti-sun products which may be in stick form. The present invention may be in the form of mascara product including mascara bars, an eyeliner product, a foundation product, a lipstick product, a blush for cheeks or eyelids, a deodorant product, a make-up product for the body, a make-up-removing product, an eyeshadow product, a face powder product, a concealer product, a treating shampoo product, a nail varnish, a hair conditioning product, a sun screen, colorant for the skin or hair, or skin care formula such as, for example, anti-pimple or shaving cut formulas. As defined herein, a deodorant product is a personal hygiene product and does not relate to care, make-up or treatment of keratin materials, including keratin fibers and nails.

For example, the composition of the present invention may be in a form chosen from a paste, a solid, a gel, and a cream. It may be an emulsion, i.e., an oil-in-water or water-in-oil emulsion, a multiple emulsion, e.g., an oil-in-water-in-oil emulsion or water-in-oil-in-water emulsion, or a solid, rigid or supple gel, including anhydrous gels. In one embodiment, the composition of the invention is anhydrous. The composition of the invention may, for example, comprise an external or continuous fatty phase. In another embodiment, the composition of the invention is transparent or clear, including for example, a composition without pigments. The composition can also be in a form chosen from a translucent anhydrous gel and a transparent anhydrous gel. The composition can also be a molded composition or cast as a stick or a dish. The composition in one embodiment is a solid such as a molded stick or a poured stick.

The structuring of the liquid fatty phase can be modified according to the nature of the polymer containing a hetero atom and of the solid substance used, and may be such that a rigid structure in the form of a rod or stick with good mechanical strength is obtained. When these rods or sticks are colored, they may make it possible, after application, to obtain a uniformly colored glossy deposit which does not migrate and which has good staying power or long-wearing properties, in particular of the color, over time. The composition may contain at least one structuring polymer and at least one solid substance.

In one embodiment, the composition of the invention is a composition for the lips such as a lipstick composition, e.g., in stick form.

Structuring Polymer

In one embodiment, the at least one structuring polymer in the composition of the invention is a solid that is not deformable at room temperature (25° C.) and atmospheric pressure (760 mmHg, i.e. 101 KPa). In a further embodiment, the at least one structuring polymer is capable of structuring the composition without opacifying it. The inventors think that is due to the fact that the polymer does not crystallize. Moreover, the structuration of the liquid phase is due to hydrogen interactions between two molecules of polymer and/or between the polymer and the liquid fatty phase. As defined above, the at least one structuring polymer of the present invention comprises a polymer skeleton comprising at least one hydrocarbon-based repeating unit comprising at least one hetero atom. In one embodiment, the at least one structuring polymer further comprises at least one terminal fatty chain chosen from alkyl and alkenyl chains, such as of at least 4 atoms, and further such as comprising 8 to 120 carbon atoms, bonded to the polymer skeleton via at least one linking group. The terminal fatty chain may, for example, be functionalized. The at least one structuring polymer may also further comprise at least one pendant fatty chain chosen from alkyl and alkenyl chains, such as of at least 4 atoms, and further such as comprising 8 to 120 carbon atoms, bonded to any carbon or hetero atom of the polymer skeleton via at least one linking group. The pendant fatty chain may, for example, be functionalized. The at least one structuring polymer may comprise both at least one pendant fatty chain and at least one terminal fatty chain as defined above, and one or both types of chains can be functionalized.

In one embodiment, the structuring polymer comprises at least two hydrocarbon-based repeating units. As a further example, the structuring polymer comprises at least three hydrocarbon-based repeating units and as an even further example, the at least three repeating units are identical.

As used herein, "functionalized" means comprising at least one functional group. Non-limiting examples of functional groups include hydroxyl groups, ether groups, oxyalkylene groups, polyoxyalkylene groups, carboxylic acid groups, amine groups, amide groups, halogen containing groups, including fluoro and perfluoro groups, halogen atoms, ester groups, siloxane groups and polysiloxane groups.

For purposes of the invention, the expression "functionalized chain" means, for example, an alkyl chain comprising at least one functional (reactive) group chosen, for example, from those recited above. For example, in one embodiment, the hydrogen atoms of at least one alkyl chain may be substituted at least partially with fluorine atoms.

According to the invention, these chains may be linked directly to the polymer skeleton or via an ester function or a perfluoro group.

For the purposes of the invention, the term "polymer" means a compound containing at least 2 repeating units, such as, for example, a compound containing at least 3 repeating units, which may be identical.

As used herein, the expression "hydrocarbon-based repeating unit" includes a repeating unit comprising from 2 to 80 carbon atoms, such as, for example, from 2 to 60 carbon atoms. The at least one hydrocarbon-based repeating unit may also comprise oxygen atoms. The hydrocarbon-based repeating unit may be chosen from saturated and unsaturated hydrocarbon-based repeating units which in turn may be chosen from linear hydrocarbon-based repeating units, branched hydrocarbon-based repeating units and cyclic hydrocarbon-based repeating units. The at least one hydrocarbon-based repeating unit may comprise, for example, at least one hetero atom that is part of the polymer skeleton, i.e., not pendant. The at least one hetero atom may be chosen, for example, from nitrogen, sulphur, and phosphorus. For example, the at least one hetero atom may be a nitrogen atom, such as a non-pendant nitrogen atom. In another embodiment, the at least one hydrocarbon-based repeating unit may comprise at least one hetero atom with the proviso that the at least one hetero atom is not nitrogen. In another embodiment, the at least one hetero atom is combined with at least one atom chosen from oxygen and carbon to form a hetero atom group. In one embodiment, the hetero atom group comprises a carbonyl group.

The at least one repeating unit comprising at least one hetero atom may be chosen, for example, from amide groups, carbamate groups, and urea groups. In one embodiment, the at least one repeating unit comprises amide groups forming a polyamide skeleton. In another embodiment, the at least one repeating unit comprises carbamate groups and/or urea groups forming a polyurethane skeleton, a polyurea skeleton and/or a polyurethane-polyurea skeleton. The pendant chains, for example, can be linked directly to at least one of the hetero atoms of the polymer skeleton. In yet another embodiment, the at least one hydrocarbon-based repeating unit may comprise at least one hetero atom group with the proviso that the at least one hetero atom group is not an amide group. In one embodiment, the polymer skeleton comprises at least one repeating unit chosen from silicone units and oxyalkylene units, the at least one repeating unit being between the hydrocarbon-based repeating units.

In one embodiment, the composition of the invention comprises at least one structuring polymer with nitrogen atoms, such as amide, urea, or carbamate units, such as amide units, and at least one polar oil.

In one embodiment, in the at least one structuring polymer, the percentage of the total number of fatty chains ranges from 40% to 98% relative to the total number of repeating units and fatty chains, and as a further example, from 50% to 95%. In a further embodiment wherein the polymer skeleton is a polyamide skeleton, in the at least one structuring polymer, the percentage of the total number of fatty chains ranges from 40% to 98% relative to the total number of all amide units and fatty chains, and as a further example, from 50% to 95%.

In a further embodiment, the nature and proportion of the at least one hydrocarbon-based repeating unit comprising at least one hetero atom depends on the nature of a liquid fatty phase of the composition and is, for example, similar to the nature of the fatty phase. For example, not to be limited as to theory, the more polar the hydrocarbon-based repeating units containing a hetero atom, and in high proportion, which corresponds to the presence of several hetero atoms, the greater the affinity of the at least one structuring polymer to polar oils. Conversely, the more non-polar, or even apolar, and lesser in proportion the hydrocarbon-based repeating units containing a hetero atom, the greater the affinity of the polymer for apolar oils.

In another embodiment, the invention is drawn to a structured composition containing at least one liquid fatty phase structured with at least one structuring polymer, wherein the at least one structuring polymer is a polyamide comprising a polymer skeleton comprising at least one amide repeating unit and optionally at least one pendant fatty chain and/or at least one terminal chain that are optionally functionalized and comprise from 8 to 120 carbon atoms, bonded to at least one of the amide repeating units via at least one linking group. The liquid fatty phase further contains at least one solid substance for hardening the liquid fatty phase. The at least one liquid fatty phase, the at least one structuring polyamide and the at least one solid substance together form a physiologically acceptable medium.

When the structuring polymer has amide repeating units, the pendant fatty chains may be linked to at least one of the nitrogen atoms in the amide repeating units.

The structuring polymer, for example the polyamide polymer, may have a weight-average molecular mass of less than 100,000, such as less than 50,000. In another embodiment, the weight-average molecular mass may range from 1000 to 30,000, such as from 2000 to 20,000, further such as from 2000 to 10,000.

However, this weight-average molecular mass can be present up to 500 000 and even up to 1 000 000.

The structuring polymer, as for example the polyamide polymer, in non soluble in water or in an aqueous phase. In another embodiment the structuring polymer has non ionic group.

As discussed, the at least one structuring polymer may, for example, be chosen from polyamide polymers. A polyamide polymer may comprise, for example, a polymer skeleton which comprises at least one amide repeating unit, i.e., a polyamide skeleton. In one embodiment, the polyamide skeleton may further comprise at least one terminal fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group, and/or at least one pendant fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group. In one embodiment, the polyamide skeleton may comprise at least one terminal fatty chain chosen from fatty chains comprising 8 to 120 carbon atoms, such as, for example, 12 to 68 carbon atoms, bonded to the at least one polyamide skeleton via at least one linking group and/or at least one pendant fatty chain chosen from fatty chains comprising 8 to 120 carbon atoms, such as, for example, 12 to 68 carbon atoms, bonded to the at least one polyamide skeleton via at least one linking group, such as bonded to any carbon or nitrogen of the polyamide skeleton via the at least one linking group. In one embodiment, the at least one linking group is chosen from single bonds and urea, urethane, thiourea, thiourethane, thioether, thioester, ester, ether and amine groups. The bond is, for example, an ester bond. In one embodiment, these polymers comprise a fatty chain at each end of the polymer skeleton, such as the polyamide skeleton.

In one embodiment, due to the presence of at least one chain, the polyamide polymers may be readily soluble in oils (i.e., water-immiscible liquid compounds) and thus may give macroscopically homogeneous compositions even with a high content (at least 25%) of the polyamide polymers, unlike certain polymers of the prior art that do not contain such alkyl or alkenyl chains at the end of the polyamide skeleton. As defined herein, a composition is soluble if it has a solubility of greater than 0.01 g per 100 ml of solution at 25° C.

In a further embodiment, the polyamide polymers can be chosen from polymers resulting from at least one polycondensation reaction between at least one acid chosen from dicarboxylic acids comprising at least 32 carbon atoms, such as 32 to 44 carbon atoms, and at least one amine chosen from diamines comprising at least 2 carbon atoms, such as from 2 to 36 carbon atoms, and triamines comprising at least 2 carbon atoms, such as from 2 to 36 carbon atoms. The at least one dicarboxylic acids can, for example, be chosen from dimers of at least one fatty acid comprising at least 16 carbon atoms, such as oleic acid, linoleic acid and linolenic acid. The at least one amine can, for example, be chosen from diamines, such as ethylenediamine, hexylenediamine, hexamethylenediamine, phenylenediamine and triamines, such as ethylenetriamine.

The polyamide polymers may also be chosen from polymers comprising at least one terminal carboxylic acid group. The at least one terminal carboxylic acid group can, for example, be esterified with at least one alcohol chosen from monoalcohols comprising at least 4 carbon atoms. For example, the at least one alcohol can be chosen from monoalcohols comprising from 10 to 36 carbon atoms. In a further embodiment, the monoalcohols can comprise from 12 to 24 carbon atoms, such as from 16 to 24 carbon atoms, and for example 18 carbon atoms.

In one embodiment, the at least one polyamide polymer may be chosen from those described in U.S. Pat. No. 5,783,657, the disclosure of which is incorporated herein by reference, which are polymers of formula (I):

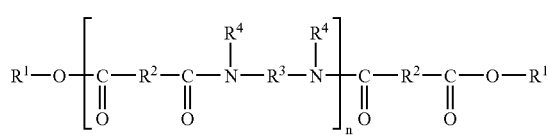

in which:

n is an integer which represents the number of amide units such that the number of ester groups present in said at least one polyamide polymer ranges from 10% to 50% of the total number of all said ester groups and all said amide groups comprised in said at least one polyamide polymer;

$R^1$, which are identical or different, are each chosen from alkyl groups comprising at least 4 carbon atoms and alkenyl groups comprising at least 4 carbon atoms. In one embodiment, the alkyl group comprises from 4 to 24 carbon atoms and the alkenyl group comprises from 4 to 24 carbon atoms;

$R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

In one embodiment, the at least one terminal fatty chain of formula (I) is linked to the last hetero atom, in this case nitrogen, of the polyamide skeleton. In a further embodiment, the terminal chains are functionalized. In another embodiment, the ester groups of formula (I), are linked to the terminal and/or pendant fatty chains, represent from 15% to 40% of the total number of ester and amide groups (i.e. heteroatom groups), such as, for example, from 20% to 35%.

In one embodiment, n may be an integer ranging from 1 to 10, for example 1 to 5, and as a further example, an integer ranging from 3 to 5. In the present invention, $R^1$, which are identical or different, can, for example, each be chosen from $C_{12}$ to $C_{22}$ alkyl groups, such as from $C_{16}$ to $C_{22}$ alkyl groups.

In the present invention, $R^2$, which are identical or different, can, for example, each be chosen from $C_{10}$ to $C_{42}$ alkyl groups. At least 50% of all $R^2$, which are identical or different, can, for example, each be chosen from groups comprising from 30 to 42 carbon atoms. At least 75% of all $R^2$, which are identical or different, can, for example, each be chosen from groups comprising from 30 to 42 carbon atoms. In the two aforementioned embodiments, the remaining $R^2$, which are identical or different, can, for example, each be chosen from $C_4$ to $C_{19}$ groups, such as $C_4$ to $C_{12}$ groups.

$R^3$, which can be identical or different, can, for example, each be chosen from $C_2$ to $C_{36}$ hydrocarbon-based groups and polyoxyalkylene groups. In another example, $R^3$, which can be identical or different, can each, for example, be chosen from $C_2$ to $C_{12}$ hydrocarbon-based groups. In another embodiment, $R^4$, which can be identical or different, can each be chosen from hydrogen atoms.

As used herein, hydrocarbon-based groups may be chosen from linear, cyclic and branched, and saturated and unsaturated groups. The hydrocarbon-based groups can be chosen from aliphatic and aromatic groups. In one example, the hydrocarbon-based groups are chosen from aliphatic groups. The alkyl and alkylene groups may be chosen from linear, cyclic and branched, and saturated and unsaturated groups.

In general, the pendant and terminal fatty chains may be chosen from linear, cyclic and branched, and saturated and unsaturated groups. The pendant and terminal fatty chains can be chosen from aliphatic and aromatic groups. In one example, the pendant and terminal fatty chains are chosen from aliphatic groups.

According to the invention, the structuring of the liquid fatty phase is obtained with the aid of at least one structuring polymer, such as the at least one polymer of formula (I). The at least one polyamide polymer of formula (I) may, for example, be in the form of a mixture of polymers, and this mixture may also comprise a compound of formula (I) wherein n is equal to zero, i.e., a diester.

Non-limiting examples of at least one polyamide polymer which may be used in the composition according to the present invention include the commercial products sold or made by Arizona Chemical under the names Uniclear 80 and Uniclear 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

Other non-limiting examples of at least one polyamide polymer which may be used in the composition according to the present invention include polyamide polymers (or polyamide resins) resulting from the condensation of at least one aliphatic dicarboxylic acid and at least one diamine, the carbonyl and amine groups being condensed via an amide bond. Examples of these polyamide polymers are those sold or made under the brand name Versamid by the companies General Mills Inc. and Henkel Corp. (Versamid 930, 744 or 1655) or by the company Olin Mathieson Chemical Corp. under the brand name Onamid, in particular Onamid S or C. These resins have a weight-average molecular mass ranging from 6000 to 9000. For further information regarding these polyamides, reference may be made to U.S. Pat. Nos. 3,645,705 and 3,148,125, the disclosures of which are hereby incorporated by reference.

Other examples of polyamides include those sold by the company Arizona Chemical under the references Uni-Rez (2658, 2931, 2970, 2621, 2613, 2624, 2665, 1554, 2623 and 2662) and the product sold or made under the reference Macromelt 6212 by the company Henkel. For further information regarding these polyamides, reference may be made to U.S. Pat. No. 5,500,209, the disclosure of which is hereby incorporated by reference. Such polyamides display high melt viscosity characteristics. MACROMELT 6212, for example, has a high melt viscosity at 190° C. of 3040 poise (as measured by a Brookfield Viscometer, Model RVF #3 spindle, 20 RPM).

In a further embodiment, the at least one polyamide polymer may be chosen from polyamide resins from vegetable sources. Polyamide resins from vegetable sources may be chosen from, for example, the polyamide resins of U.S. Pat. Nos. 5,783,657 and 5,998,570, the disclosures of which are herein incorporated by reference.

The at least one structuring polymer in the composition of the invention may have a softening point greater than 50° C., such as from 65° C. to 190° C., and preferably less than 150° C., and further such as from 70° C. to 130° C., and even further such as from 80° C. to 105° C. This softening point may be lower than that of structuring polymers used in the art which may facilitate the use of the at least one structuring polymer of the present invention and may limit the degradation of the liquid fatty phase. These polymers may be non waxy polymers. The softening point can be measured by a well known method as "Differential Scanning Calorimetry (i.e. DSC method) with a temperature rise of 5 to 10° C./min.

In one embodiment, the at least one polyamide polymer may be present in the composition in an amount ranging, for example, from 0.5% to 80%, such as from 2% to 60%, further such as from 5% to 40%, by weight relative to the total weight of the composition. In a further embodiment the at least one polyamide polymer may be present in the composition in an amount ranging, for example, from 5% to 25% by weight relative to the total weight of the composition.

In one embodiment, the at least one structuring polymer in the composition according to the invention corresponds to the polyamide polymers of formula (I). Due to fatty chain(s), these polymers may be readily soluble in oils and thus lead to compositions that are macroscopically homogeneous even with a high content (at least 25%) of at least one structuring polymer.

In one embodiment, when the at least one structuring polymer of the present invention comprises a urea urethane having the following formula:

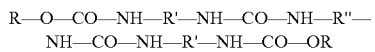

then R represents $C_nH_{2n+1}$—, wherein n represents an integer having a value greater than 22, for example from 23 to 120, and further, for example, from 23 to 68, or $C_mH_{2m+1}(OC_pH_{2p})_r$—, wherein m represents an integer having a value of greater than 18, for example, from 19 to 120, and further, for example, from 23 to 68, p represents an integer having a value of from 2 to 4, and r represents an integer having a value of from 1 to 10.

R' represents:

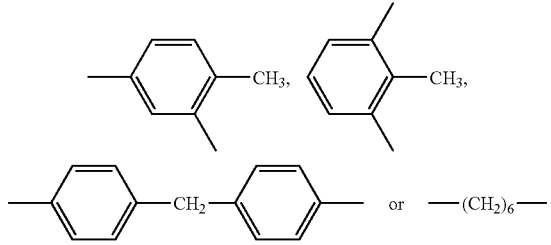

and R" represents:

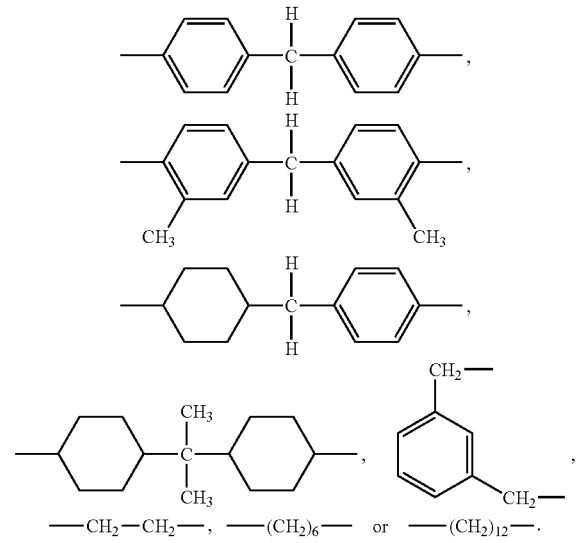

In another embodiment of the invention, the at least one structuring polymer is not a urea urethane of the formula:

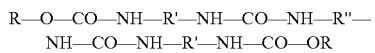

wherein R represents $C_nH_{2n+1}$— or $C_mH_{2m+1}(C_pH_{2p}O)_r$—; n represents an integer having a value of from 4 to 22; m represents an integer having a value of from to 18; p represents an integer having a value of from 2 to 4; and r represents an integer having a value of from 1 to 10.

R' represents:

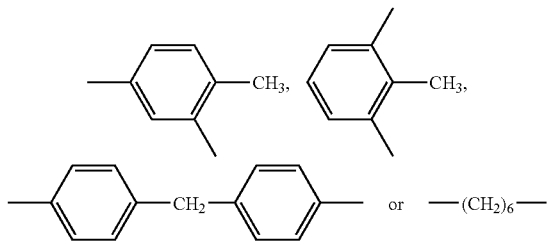

and R" represents:

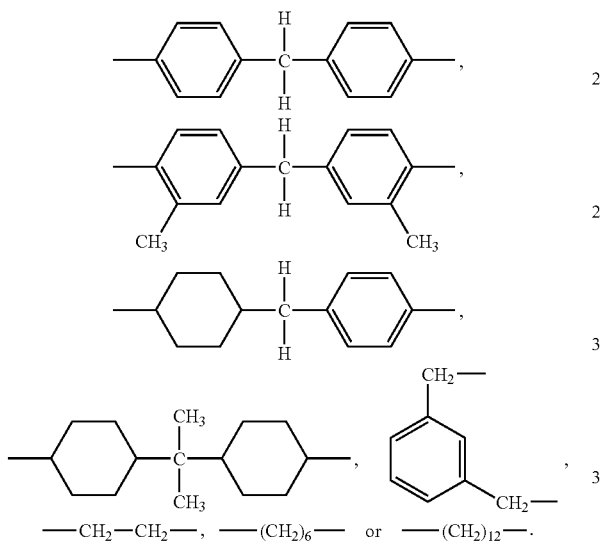

In another embodiment, the present invention is drawn to a structured composition comprising at least one solid substance that has a melting point of about 45° C., for example about 47° C., or greater, and at least one liquid fatty phase structured with at least one structuring polymer comprising a polymer skeleton comprising at least one hydrocarbon-based repeating unit comprising at least one hetero atom, wherein the at least one structuring polymer further comprises at least one terminal fatty chain, optionally functionalized, chosen from alkyl chains and alkenyl chains, wherein said at least one terminal fatty chain is bonded to said polymer skeleton via at least one linking group chosen from amides, ureas, and esters, wherein when said at least one linking group is chosen from esters, said at least one terminal fatty chain is chosen from branched alkyl groups. The at least one structuring polymer may also comprise at least one pendant fatty chain, optionally functionalized, chosen from alkyl chains and alkenyl chains, bonded to any carbon or hetero atom of the polymer skeleton via at least one linking group chosen from amides, ureas, and esters, wherein when said at least one linking group is chosen from esters, said at least one pendant fatty chain is chosen from branched alkyl groups. The at least one structuring polymer may comprise both at least one pendant fatty chain and at least one terminal fatty chain as defined above in this paragraph.

Further, an embodiment of the invention relates to a skin lip, or keratinous fiber care or make-up composition comprising a structured composition containing at least one liquid fatty phase structured with at least one structuring polymer comprising a polymer skeleton comprising at least one hydrocarbon-based repeating unit comprising at least one hetero atom and at least one solid substance that has a melting point of about 45° C., for example about 47° C., or greater. In another embodiment, the invention relates to a lipstick composition in stick form comprising at least one continuous liquid fatty phase, at least one solid substance that has a melting point of about 45° C., for example, about 47° C. or greater, and at least one non-waxy structuring polymer having a weight-average molecular mass of less than 100,000.

Additionally, an embodiment of the invention relates to a skin, lip, or keratinous fiber care or make-up composition comprising a structured composition containing at least one liquid fatty phase structured with at least one structuring polymer comprising a polymer skeleton comprising at least one hydrocarbon-bated repeating unit comprising at least one hetero atom, at least one solid substance that has a melting point of about 45° C., for example about 47° C., or greater, and at least one coloring agent.

Additionally, an embodiment of the invention relates to a method of making up skin, lips, or keratinous fibers or caring for skin, lips, or keratinous fibers comprising applying to said skin, lips, or keratinous fibers a structured composition containing at least one liquid fatty phase structured with at least one structuring polymer comprising a polymer skeleton comprising at least one hydrocarbon-based repeating unit comprising at least one hetero atom and at least one solid substance that has a melting point of about 45° C., for example about 47° C., or greater.

Solid Substance with a Melting Point of about 45° C. or Greater

As defined here, a solid substance having a melting point of about 45° C. or greater is a compound that is a solid at room temperature (25° C.) ras and undergoes a reversible solid/liquid change of state at about 45° C., for example about 47° C., or greater, and at atmospheric pressure (760 mmHg, i.e. 101 KPa). The at least one solid substance may, for example, have a melting point of about 50° C. or greater. In one embodiment, the at least one solid substance is an organic solid substance having a melting point of about 45° C., for example about 47° C., or greater.

Such compounds are rheological agents, for example non tinted rheological agents. Such compounds include, but are not limited to, waxes, fillers, glitters, and solid polymers. In one embodiment, a filler is chosen from powders, polyamide (Nylon®), polymethylthacrylate (PMMA) crosspolymers, and silicas. In a further embodiment, the solid substance has a melting point of about 50° C. to about 250° C., such as from about 60° C. to about 200° C. A solid substance for use in the practice of the invention may comprise at least one crystallizable portion, however crystallization is not a limitation. The melting point is measured by DSC (Differential Scanning Calorimetry) with a rate of increase in temperature of 5° C. or 10° C. per minute. The melting point corresponds to the peak of the DSC curve.

In one embodiment, the solid substance is a wax. As used herein, a "wax" may be any lipophilic fatty compound. It may be possible to make a wax miscible with oils by bringing the wax to its melting point, and, thereby, to form a microscopically homogeneous mixture, but once the mixture has returned to room temperature, recrystallization of the wax occurs.

For the purposes of the invention, waxes may be chosen from any wax that meets the criteria described herein. Non-limiting examples of such waxes include waxes of natural origin, such as beeswax, carnauba wax, candelilla wax, ouricury wax, Japan wax, cork fiber wax, sugar cane wax, paraffin waxes, lignite wax, microcrystalline waxes, lanolin wax, montan wax and ozokerites, hydrogenated oils such as hydrogenated jojoba oil, waxes of synthetic origin, such as polyethylene waxes derived from polymerization or copolymerization of ethylene, waxes obtained by Fischer-Tropsch synthesis, tetrastearate di-(trimethylol-1,1,1 propane) as the one sold or made under the name HEST 2T-4S by Heterene, fatty acid esters and glycerides, and silicone waxes, such as derivatives of poly(di)methylsiloxane, including esterified silicon waxes.

For the purposes of the invention, solid polymer serving as rheological agent is any lipophilic polymeric fatty compound. It may be possible to make a solid polymer miscible with oils by bringing the solid polymer to its melting point, and, thereby, to form a microscopically homogeneous mixture, but once the mixture has returned to room temperature, solidification of the mixture (solid polymer+oils) occurs for example by recrystallization of the solid polymer.

In one embodiment, the solid polymer serving as rheological agent is an organic semi-crystallized polymer comprising a) a polymeric skeleton and b) at least one organic crystallizable side-chain or at least one organic crystallizable sequence which is a part of said skeleton. In one embodiment, this solid polymer has a weight-average molecular mass more than 2 000 and less than 100 000. For example, this solid polymer has a weight-average molecular mass from 4 000 to 99 000.

In one embodiment, the solid polymer serving as rheological agent is chosen from homopolymers or copolymers having at least one side-chain crystallizable, such as those disclosed in the U.S. Pat. No. 5,156,911, disclosure of which is herein incorporated by reference.

The concentrations of the at least one solid substance and of the at least one structuring polymer may be chosen according to the desired hardness and desired stability of the compositions and according to the specific application envisaged. The respective concentrations of the at least one structuring polymer and of the at least one solid substance can be such that a disintegrable solid which does not flow under its own weight is obtained.

Depending on the intended application, such as a stick, hardness of the composition may also be considered. The hardness of a composition may, for example, be expressed in grams (g). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into said composition and in particular using a texture analyzer (for example TA-XT2i from Rhéo) equipped with an ebonite cylinder of height 25 mm and diameter 8 mm. The hardness measurement is carried out at 20° C. at the center of 5 samples of said composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method OSI which involves cutting an 8.1 mm or preferably 12.7 mm in diameter of composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, and further such as from 30 gf to 200 gf.

The hardness of the composition of the present invention may be such that the compositions are self-supporting and can easily disintegrate to form a satisfactory deposit on a keratinous material. In addition, this hardness may impart good impact strength to the inventive compositions which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within the scope of the invention.

According to the present invention, the compositions in stick form may also possess the properties of deformable, flexible elastic solids and may also have noteworthy elastic softness upon application to a keratinous material. The compositions in stick form of the prior art do not have this elasticity and flexibility.

The at least one structuring polymer may be present in a concentration ranging from 0.5% to 80% by weight of the total weight of the composition, such as from 5% to 40%. The at least one solid substance may be present in a concentration of at least 3% by weight of the total weight of the composition, such as, for example, greater than 5%; further examples include from 5% to 70% by weight of the total weight of the composition, from 10% to 60% and from 10% to 50%.

Liquid Fatty Phase

The at least one liquid fatty phase, in one embodiment, may comprise at least one oil. In one embodiment, at least one oil has an affinity with the structuring polymer and/or with the solid substance. The at least one oil, for example, may be chosen from polar oils and apolar oils including hydrocarbon-based liquid oils and oily liquids at room temperature. In one embodiment, the composition of the invention comprises at least one structuring polymer and at least one polar oil. The polar oils of the invention, for example, may be added to the apolar oils, the apolar oils acting in particular as co-solvent for the polar oils.

According to the invention, the structuring of the at least one liquid fatty phase may, for example, be obtained with the aid of at least one polymer of formula (I). In general, the polymers of formula (I) may be in the form of mixtures of polymers, these mixtures also possibly containing a synthetic product corresponding to a compound of formula (I) in which n is 0, i.e., a diester.

The liquid fatty phase of the composition may contain more than 30%, for example, more than 40%, of liquid oil(s) containing a group similar to that of the units containing a hetero atom of the structuring polymer, and for example from 50% to 100%. In one embodiment, the liquid fatty phase structured with a polyamide-type skeleton contains a high quantity, i.e., greater than 30%, for example greater than 40% relative to the total weight of the liquid fatty phase, or from 50% to 100%, of at least one apolar, such as hydrocarbon-based, oil. For the purposes of the invention, the expression "hydrocarbon-based oil" means an oil essentially comprising carbon and hydrogen atoms, optionally with at least one group chosen from hydroxyl, ester, carboxyl, or ether groups.

For a liquid fatty phase structured with a polymer containing a partially silicone-based skeleton, this fatty phase may contain more than 30%, for example, more than 40%, relative to the total weight of the liquid fatty phase and, for example, from 50% to 100%, of at least one silicone-based liquid oil, relative to the total weight of the liquid fatty phase.

For a liquid fatty phase structured with an apolar polymer of the hydrocarbon-based type, this fatty phase may contain more than 30%, for example more than 40% by weight, or from 50% to 100% by weight, of at least one liquid apolar, such as hydrocarbon-based, oil, relative to the total weight of the liquid fatty phase.

For example, the at least one polar oil useful in the invention may be chosen from:

hydrocarbon-based plant oils with a high content of triglycerides comprising fatty acid esters of glycerol in which the fatty acids may have varied chain lengths from $C_4$ to $C_{24}$, these chains possibly being chosen from linear and branched, and saturated and unsaturated chains; these oils are chosen from, for example, wheat germ oil, corn oil, sunflower oil, karite butter, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grape seed oil, blackcurrant seed oil, evening primrose oil, millet oil, barley oil, quinoa oil, olive oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic oils or esters of formula $R_5COOR_6$ in which $R_5$ is chosen from linear and branched fatty acid residues containing from 1 to 40 carbon atoms and $R_6$ is chosen from, for example, a hydrocarbon-based chain containing from 1 to 40 carbon atoms, on condition that $R_5+R_6 \geqq 10$, such as, for example, purcellin oil (cetostearyl octanoate), isononyl isononanoate, $C_{12}$-$C_{15}$ alkyl benzoates, isopropyl myristate, 2-ethylhexyl palmitate, isostearyl isostearate and alkyl or polyalkyl octanoates, decanoates or ricinoleates; hydroxylated esters such as isostearyl lactate and diisostearyl malate; and pentaerythritol esters;

synthetic ethers containing from 10 to 40 carbon atoms;

$C_8$ to $C_{26}$ fatty alcohols such as oleyl alcohol; and $C_8$ to $C_{26}$ fatty acids such as oleic acid, linolenic acid or linoleic acid.

The at least one apolar oil according to the invention is chosen from, for example, silicone oils chosen from volatile and non-volatile, linear and cyclic polydimethylsiloxanes (PDMSs) that are liquid at room temperature; polydimethylsiloxanes comprising alkyl or alkoxy groups which are pendant and/or at the end of the silicone chain, the groups each containing from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates; hydrocarbons chosen from linear and branched, volatile and non-volatile hydrocarbons of synthetic and mineral origin, such as volatile liquid paraffins (such as isoparaffins and isododecane) or non-volatile liquid paraffins and derivatives thereof, liquid petrolatum, liquid lanolin, polydecenes, hydrogenated polyisobutene such as hydrogenated polybutene, e.g., Parleam® from Nippon Oil Fats and squalane; and mixtures thereof. The structured oils, for example those structured with polyamides such as those of formula (I) or the polyurethanes or polyureas or polyureaurethanes, may be, in one embodiment, apolar oils, such as an oil or a mixture of hydrocarbon oils chosen from those of mineral and synthetic origin, chosen from hydrocarbons such as alkanes such as Parleam® oil, isoparaffins including isododecane, and squalane, and mixtures thereof. These oils may, in one embodiment, be combined with at least one phenyl-silicone oil.

The liquid fatty phase, in one embodiment, contains at least one non-volatile oil chosen from, for example, hydrocarbon-based oils of mineral, plant and synthetic origin, synthetic esters or ethers, silicone oils and mixtures thereof.

In practice, the total liquid fatty phase may be present, for example, in an amount ranging from 1% to 99% by weight relative to the total weight of the composition; further examples include ranges of 5% to 99%, 5% to 95.5%, 10% to 80%, and 20% to 75%.

For the purposes of the invention, the expression "volatile solvent or oil" means any non-aqueous medium capable of evaporating on contact with the skin or the lips in less than one hour at room temperature and atmospheric pressure. The volatile solvent(s) of the invention is(are) organic solvents, such as volatile cosmetic oils that are liquid at room temperature, having a non-zero vapor pressure, at room temperature and atmospheric pressure, ranging in particular from $10^{-2}$ to 300 mmHg (1.33 to 40 000 Pa) and, for example, greater than 0.03 mmHg (40 Pa) and for example greater than 0.3 mmHg (40 Pa). The expression "non-volatile oil" means an oil which remains on the skin or the lips at room temperature and atmospheric pressure for at least several hours, such as those having a vapor pressure of less than $10^{-2}$ mmHg (1.33 Pa).

According to the invention, these volatile solvents may facilitate the staying power or long wearing properties of the composition on the skin, the lips or superficial body growths such as nails and keratineous fibers. The solvents can be chosen from hydrocarbon-based solvents, silicone solvents optionally comprising alkyl or alkoxy groups that are pendant or at the end of a silicone chain, and a mixture of these solvents.

The volatile oil(s), in one embodiment, is present in an amount ranging from 0% to 95.5% relative to the total weight of the composition, such as from 2% to 75% or, for example, from 10% to 45%. This amount will be adapted by a person skilled in the art according to the desired staying power or long wearing properties.

In one embodiment, the compositions of the invention are anhydrous. The at least one liquid fatty phase of the composition of the invention may further comprises a dispersion of lipid vesicles. The composition of the invention may also, for example, be in the form of a fluid anhydrous gel, a rigid anhydrous gel, a fluid simple emulsion, a fluid multiple emulsion, a rigid simple emulsion or a rigid multiple emulsion. The simple emulsion or multiple emulsion may comprise a continuous phase chosen from an aqueous phase optionally containing dispersed lipid vesicles, or a fatty phase optionally containing dispersed lipid vesicles. In one embodiment, the composition has a continuous oily phase or fatty phase and is more specifically an anhydrous composition, for example, a stick or dish form. An anhydrous composition is one that has less than 10% water by weight, such as, for example, less than 5% by weight.

Additional Additive

The compositions of the invention may further comprise at least one additional fatty material. The at least one additional fatty material may, for example, be chosen from gums, liposoluble or lipodispersible gelling agents, fatty materials pasty or viscous at ambient temperature, and resins.

The composition of the present invention may also further comprise at least one suitable additive commonly used in the field concerned chosen from coloring agents, antioxidants, essential oils, preserving agents, fragrances, neutralizing agents, liposoluble polymers, dispersants and cosmetically active agents and dermatological active agents such as, for example, emollients, moisturizers, vitamins, essential fatty acids and sunscreens, and mixtures thereof. The at least one additive is generally present in a concentration ranging up to 20% by weight of the total weight of the composition, such as up to 10%, for example from 0.01 to 10%. The compositions of the present invention may also further comprise water, water, optionally thickened with an aqueous-phase thickener, or gelled with a hydrophilic gelling agent and/or containing ingredients soluble in water. The water can represents form 0.01% to 50% for example from 0.5% to 30% relative to the total weight of the composition.

The composition can also contains at least one active agent, i.e. an agent having a beneficial effect on the skin, lips or body growths.

Needless to say, the person skilled in the art will take care to select the optional additional additives and the amount thereof such that at least one advantageous property of the composition according to the invention, such as stability, non-migration, is not, or is not substantially, adversely affected by the addition(s) envisaged.

The composition according to the invention can be in the form of a tinted or non tinted care composition for keratin materials such as the skin, the lips and superficial body growths. Then it can be used, for example, as a care base for the skin, superficial body growths or the lips, for example, lips balms for protecting the lips against cold and/or sunlight and/or wind, or care cream for the skin (body and face).

The composition of the invention may be also in the form of a colored make-up product for the skin, such as a foundation, an eyeshadow, a concealer, an eyeliner, a make-up for the body; a make-up for the lips such as lipgloss or lipstick; a make-up for eyelashes, for example in a form of mascara cake, or for the eyebrows, for example in the form of pencil.

The compositions of the invention may also comprise at least one coloring agent chosen from pigments, dyes, nacreous pigments (i.e. nacres), and pearling agents. The at least one coloring agent may be chosen, for example, in order to obtain make-up compositions which give good coverage, that is, which do not leave a significant amount of the at least one keratin material to which it is applied showing through. The pigments may also reduce the sticky feel of the compositions, unlike soluble dyes.

Representative liposoluble dyes which may be used according to the present invention include Sudan red, DC Red 17, DC Green 6, β-carotene, soybean oil, Sudan brown, DC Yellow 11, DC Violet 2, DC Orange 5, annatto, and quinoline yellow. The liposoluble dyes, when present, generally have a concentration ranging up to 20% by weight of the total weight of the composition, such as from 0.1% to 6%.

The pigments which may be used according to the present invention may be chosen from white, colored, mineral, organic, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate and ferric blue. Representative examples of organic pigments include carbon black, pigments of D & C type, and lakes based on cochineal carmine, barium, strontium, calcium and aluminum. If present, the pigments may have a concentration ranging up to 40% by weight of the total weight of the composition, and for example up to 50%, such as from 1% to 35%, and further such as from 2% to 25%. In the case of a face powder product, the pigments, including nacreous pigments, may, for example, represent up to 90% by weight of the composition.

The nacreous pigments (or nacres) which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacres, if present, may have a concentration ranging up to 30% by weight of the total weight of the composition, such as from 0.1% to 20%.

In one embodiment, the coloring agents is a pigment (nacreous or not).

The composition according to the present invention may be manufactured by one of ordinary skill in the art. For example, they may be manufactured by a process which comprises heating the at least one structuring polymer at least to its softening point, adding the at least one solid substance, in one embodiment in a melted form, and any suitable additives, if present, to the at least one structuring polymer followed by mixing the composition. The resultant homogeneous mixture may then be cast or poured in a suitable mold such as a lipstick mold, foundation mold, or deodorant mold or cast directly into the packaging articles such as a case or a dish.

The present invention is also directed to a cosmetic process for caring for, making up or treating a keratin material, such as that of a human being, and further such as human skin, lips, hair, eyebrows, nails, and eyelashes, comprising the application to a keratin material of a cosmetic composition comprising a liquid fatty phase comprising at least one structuring polymer, as defined herein, such as at least one structuring polymer comprising a polyamide skeleton. The polyamide skeleton comprises at least one end group with at least one chain chosen from alkyl chains comprising at least four carbon atoms and alkenyl chains comprising at least four carbon atoms, bonded to the at least one polyamide skeleton via at least one linking group. The polyamide skeleton may comprise at least one pendant group with at least one chain chosen from alkyl chains, for example, alkyl chains comprising at least four carbon atoms, and alkenyl chains, for example, alkenyl chains comprising at least four carbon atoms, bonded to any carbon or nitrogen of the polyamide skeleton via at least one linking group. The polyamide skeleton may also comprise at least one said end group and at least one said pendant group. The at least one structuring polymer is present in an amount effective to provide structure to said fatty phase. The composition further comprises at least one solid substance that has a melting point of about 45° C., for example about 47° C., or greater. The at least one structuring polymer and the at least one solid substance are present in a combined amount to provide the composition with stability, as previously defined herein.

In another embodiment, the present invention is directed to a process of making a cosmetic composition in the form of a physiologically acceptable composition comprising including in said composition at least one liquid fatty phase, said at least one liquid fatty phase being structured with at least one structuring polymer composition comprising a polyamide skeleton. The polyamide skeleton comprises at least one end group with at least one chain chosen from alkyl chains, for example alkyl chains comprising at least four carbon atoms and alkenyl chains, for example alkenyl chains comprising at least four carbon atoms, bonded to the at least one polyamide skeleton via at least one linking group. The polyamide skeleton may further comprise at least one pendant group with at least one chain chosen from alkyl chains, for example, alkyl chains comprising at least four carbon atoms and alkenyl chains, for example alkenyl chains comprising at least four carbon atoms, bonded to any carbon or nitrogen of the polyamide skeleton via at least one linking group. The at least one structuring polymer is present in an amount effective to provide structure to said fatty phase. The composition further comprises at least one solid substance that has a melting point of about 45° C., for example about 47° C., or greater. The at least one structuring polymer and the at least one solid substance are present in a combined amount to provide the composition with stability, as previously defined herein.

The invention will be illustrated by, but is not intended to be limited to, the following examples. The amount are given a percentage by mass.

EXAMPLE 1

Anhydrous Compact Foundation

An anhydrous compact composition was prepared using the following ingredients.

| | |
|---|---|
| Isostearyl Neopentanoate | qsp 100% |
| Isononyl Isononanoate | 15% |
| Iron Oxides | 3.4% |
| Titanium Dioxide Anatase Form | 10.6% |
| Methylparaben | 0.2% |
| Talc | 8.3% |
| Kaolin | 3% |
| Titanium Dioxide treated with Dimethicone | 5% |
| Polyethylene wax MW 500 (weight avg. molecular weight) | 5.7% |
| Uniclear 100 | 7.4% |
| Polymethyl Methacrylate | 4% |
| PTFE | 4% |
| Octyldodecanol | 4.4% |

Preparation: The Uniclear 100 was solubilized (or dissolved), at 100° C., in a mixture of melted oils and wax, followed by addition of the pigments and fillers. The whole was mixed using a deflocculating turbomixer (Raynerie).

The stability of the composition was tested using the test described herein. The composition was found to have good stability in that there was no exudation at room temperature, at 45° C. and at 47° C., both at one month and at eight weeks.

EXAMPLE 2

Lip Stick

A lip stick composition was prepared using the following ingredients.

| | |
|---|---|
| Isononyl Isononanoate | qsp 100% |
| Uniclear 100 | 15% |
| Diisostearyl Malate | 12% |
| Polyethylene wax | 12% |
| Polyglyceryl-2 Diisostearate | 5.9% |
| Iron Oxides | 4% |
| Nylon-12 | 4% |
| Red 7 Lake | 1.8% |
| Titanium Dioxide | 1.2% |
| Barium Sulfate | 0.6% |
| Rosin/Colophonium | 0.6% |

Preparation: The Uniclear 100 was solubilized (or dissolved), at 100° C., in a mixture of melted oils and wax, followed by addition of the pigments and fillers. The whole was mixed using a deflocculating turbomixer (Raynerie) and then case in lipstick molds.

The stability of the composition was tested using the test described herein. The composition was found to have good stability in that there was no exudation at room temperature, at 45° C. and at 47° C., both at one month and at eight weeks.

EXAMPLE 3

Lip Stick

A lip stick composition was prepared using the following ingredients.

| | |
|---|---|
| PHASE A | |
| Uniclear 100 | 16% |
| Carnauba wax | 13% |
| Isononyl isonononanoate | 13% |
| Di-isostearylmalate | 9% |
| PHASE B | |
| Hydrophobic silica | 3% |
| Hydrogenated poly isobutene | 10.36% |
| Actyldodecanol | 3.52% |
| PHASE C | |
| Pigments | 12% |
| Liquid lanolin | 14% |
| Hydrogenated poly isobutene | 4.64% |
| Octyldodecanol | 1.48% |

Procedure: The Uniclear 100 and the oils of phase A were introduced into a heating vessel. The mixture was placed under magnetic stirring and then heated in a first stage to 100° C. (to liquefy the Uniclear). A mixture comprising the silica gel (phase B), prepared beforehand, and the ground pigmentary material (phase C), which was heated beforehand to 100° C. and homogenized with stirring, was introduced. The product obtained was placed in a heated mold (T°=45° C.) with stirring and, once setting had begun, was placed in a freezer (T°=−21° C.) for 15 minutes.

a) Silica Gel (Phase B)

The gel was prepared, with stirring, in a Rayneri stirrer at 60° C., using a hotplate, by introducing the silica portionwise into the oily mixture formed from the other phase B ingredients b) Ground Pigmentary Material (Phase C)

The pigments were mixed with the oil heated to 60° C.; the mixture was ground 3 times in a three-roll mill.

The sticks of lipstick had a hardness of 86±5 gf measured using a "cheese wire". These sticks of lipstick broke during the measurement of the dynamic fragility carried out on 3 sticks. The fragility of the composition is determined by a method wherein the stick is submitted to several back-and-forth movements on a support for 3 minutes at a speed of 60 back-and-forth movements/minute, at 20° C. The result is defined by the number of broken sticks with respect to the number of tested sticks.

We claim:

1. A cosmetic composition comprising:
   (i) at least one liquid fatty phase structured by at least one polymer;
   (ii) at least one structuring polymer chosen from polymers of following formula (I):

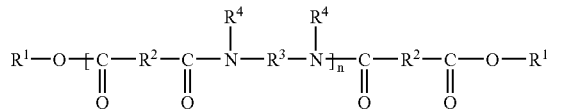

(I)

in which n is an integer which represents the number of amide units such that the number of ester groups present in said at least one structuring polymer ranges from 10% to 50% of the total number of all said ester groups and all said amide groups comprised in said at least one structuring polymer;

R1, which are identical or different, are each chosen from alkyl groups with at least 4 carbon atoms and alkenyl groups with at least 4 carbon atoms;

R2, which are identical or different, are each chosen from C4 to C42 hydrocarbon-based groups with the proviso that at least 50% of R2 are chosen from C30 to C42 hydrocarbon-based groups;

R3, which are identical or different, are each chosen from organic groups provided with at least 2 carbon atoms, with hydrogen atoms and optionally with one or more oxygen or nitrogen atoms; an—R4, which are identical or different, are each chosen from hydrogen, C1 to C10 alkyl groups, and direct bonds to R3 or another R4, so that the nitrogen atom to which both R3 and R4 are bonded forms part of a heterocyclic structure defined by R4-N—R3, with at least 50% of the R4 groups representing a hydrogen atom; and (iii) at least one esterified silicon wax having a melting point of about 45° C. or greater.

2. A cosmetic composition comprising:
   (i) at least one liquid fatty phase structured by at least one polymer;
   (ii) at least one structuring polymer chosen from polymers of following formula (I):

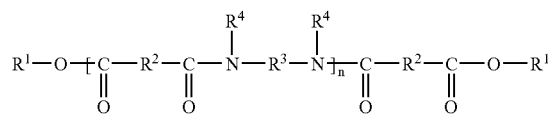

(I)

in which n is an integer which represents the number of amide units such that the number of ester groups present in said at least one structuring polymer ranges from 10% to 50% of the total number of all said ester groups and all said amide groups comprised in said at least one structuring polymer;

R1, which are identical or different, are each chosen from alkyl groups with at least 4 carbon atoms and alkenyl groups with at least 4 carbon atoms;

R2, which are identical or different, are each chosen from C4 to C42 hydrocarbon-based groups with the proviso that at least 50% of R2 are chosen from C30 to C42 hydrocarbon-based groups;

R3, which are identical or different, are each chosen from organic groups provided with at least 2 carbon atoms, with hydrogen atoms and optionally with one or more oxygen or nitrogen atoms; an—R4, which are identical or different, are each chosen from hydrogen, C1 to C10 alkyl groups, and direct bonds to R3 or another R4, so that the nitrogen atom to which both R3 and R4 are bonded forms part of a heterocyclic structure defined by R4-N—R3, with at least 50% of the R4 groups representing a hydrogen atom; and (iii) at least one organic semi-crystallized polymer having a melting point of about 45° C. or greater.

* * * * *

UNITED STATES PATENT AND TRADEMARK OFFICE
CERTIFICATE OF CORRECTION

| | |
|---|---|
| PATENT NO. | : 7,491,749 B2 |
| APPLICATION NO. | : 10/182830 |
| DATED | : February 17, 2009 |
| INVENTOR(S) | : Roberto Cavazzuti et al. |

It is certified that error appears in the above-identified patent and that said Letters Patent is hereby corrected as shown below:

Title page, item (75) ("Inventors"), line 1,
"Roberto Cavazzuti, Westfield, NJ (US);" should read
--Roberto Cavazzuti, Paris (FR);--.

Title page, item (75) ("Inventors"), lines 4-5,
"Carlos O. Pinzon, Hackensack, NJ (US);" should read
--Carlos O. Pinzon, New Milford, NJ (US);--.

Claim 1, col. 21, line 30, "R1" should read --$R^1$--.

Claim 1, col. 21, line 33, "R2" should read --$R^2$--.

Claim 1, col. 21, line 34, "C4 to C42" should read --$C_4$ to $C_{42}$--.

Claim 1, col. 21, line 35, "R2" should read --$R^2$--.

Claim 1, col. 21, lines 35-36, "C30 to C42" should read --$C_{30}$ to $C_{42}$--.

Claim 1, col. 21, line 37, "R3" should read --$R^3$--.

Claim 1, col. 21, line 40, "an —R4" should read --and $R^4$--.

Claim 1, col. 21, line 42, "C1 to C10" should read --$C_1$ to $C_{10}$--.

Claim 1, col. 21, lines 42-43, "R3 or another R4" should read --$R^3$ or another $R^4$--.

Claim 1, col. 21, line 44, "R3 and R4" should read --$R^3$ and $R^4$--.

Claim 1, col. 22, line 1, "R4-N—R3" should read --$R^4$–N–$R^3$--.

Claim 1, col. 22, line 2, "R4" should read --$R^4$--.

Claim 2, col. 22, line 25, "R1" should read --$R^1$--.

Claim 2, col. 22, line 28, "R2" should read --$R^2$--.

Claim 2, col. 22, line 29, "C4 to C42" should read --$C_4$ to $C_{42}$--.

UNITED STATES PATENT AND TRADEMARK OFFICE
CERTIFICATE OF CORRECTION

PATENT NO.       : 7,491,749 B2
APPLICATION NO.  : 10/182830
DATED            : February 17, 2009
INVENTOR(S)      : Roberto Cavazzuti et al.

It is certified that error appears in the above-identified patent and that said Letters Patent is hereby corrected as shown below:

Claim 2, col. 22, line 30, "R2" should read --$R^2$--.

Claim 2, col. 22, lines 30-31, "C30 to C42" should read --$C_{30}$ to $C_{42}$--.

Claim 2, col. 22, line 32, "R3" should read --$R^3$--.

Claim 2, col. 22, line 35, "an —R4" should read --and $R^4$--.

Claim 2, col. 22, line 37, "C1 to C10" should read --$C_1$ to $C_{10}$--.

Claim 2, col. 22, lines 37-38, "R3 or another R4" should read --$R^3$ or another $R^4$--.

Claim 2, col. 22, line 39, "R3 and R4" should read --$R^3$ and $R^4$--.

Claim 2, col. 22, line 40, "R4-N—R3" should read --$R^4$–N–$R^3$--.

Claim 2, col. 22, line 41, "R4" should read --$R^4$--.

Signed and Sealed this

Twenty-first Day of April, 2009

JOHN DOLL
*Acting Director of the United States Patent and Trademark Office*